United States Patent
Uesugi et al.

(10) Patent No.: US 8,840,580 B2
(45) Date of Patent: *Sep. 23, 2014

(54) SYSTEM AND METHOD FOR SUPPLYING PREDETERMINED GAS AT TWO DIFFERENT PRESSURE VALUES

(75) Inventors: Takefumi Uesugi, Tokyo (JP); Daisuke Sano, Tokyo (JP); Atsuhiko Kasahi, Yokohama (JP); Kenji Noda, Tokyo (JP)

(73) Assignee: Olympus Corporation (JP)

( * ) Notice: Subject to any disclaimer, the term of this patent is extended or adjusted under 35 U.S.C. 154(b) by 400 days.

This patent is subject to a terminal disclaimer.

(21) Appl. No.: 11/093,600

(22) Filed: Mar. 30, 2005

(65) Prior Publication Data
US 2005/0222534 A1    Oct. 6, 2005

(30) Foreign Application Priority Data
Mar. 30, 2004   (JP) ................ 2004-100592

(51) Int. Cl.
| | | |
|---|---|---|
| *A61M 37/00* | (2006.01) | |
| *A61M 1/00* | (2006.01) | |
| *A61M 31/00* | (2006.01) | |
| *A61M 13/00* | (2006.01) | |
| *A61B 19/02* | (2006.01) | |
| *A61B 17/34* | (2006.01) | |

(52) U.S. Cl.
CPC .......... *A61M 13/003* (2013.01); *A61B 17/3474* (2013.01); *A61B 19/0248* (2013.01); *A61B 2019/025* (2013.01)
USPC ................ 604/26; 604/30; 600/560

(58) Field of Classification Search
CPC . A61M 13/00; A61M 13/003; A61M 13/006; A61M 2205/3344; A61M 2205/3334; A61M 2202/02; A61M 2202/0025; A61M 2210/1021; A61M 2210/1017; A61M 2210/106; A61M 2210/1064; A61B 17/3474
USPC ............... 604/19, 23–26, 30–35, 65–67, 118, 604/131; 600/560
See application file for complete search history.

(56) References Cited

U.S. PATENT DOCUMENTS

| | | | | |
|---|---|---|---|---|
| 5,006,109 | A  * | 4/1991 | Douglas et al. ................. | 604/26 |
| 5,246,419 | A  * | 9/1993 | Absten ............................. | 604/26 |
| 5,328,458 | A  * | 7/1994 | Sekino et al. ................... | 604/26 |
| 6,299,592 | B1 * | 10/2001 | Zander ............................ | 604/26 |
| 6,537,495 | B1 * | 3/2003 | Cambron et al. ............... | 422/45 |
| 7,702,223 | B2 * | 4/2010 | Qian et al. ..................... | 388/825 |
| 7,722,559 | B2 * | 5/2010 | Uesugi et al. .................. | 604/26 |
| 7,981,072 | B2 * | 7/2011 | Uesugi et al. .................. | 604/23 |
| 2004/0153027 | A1 * | 8/2004 | Mantell ........................... | 604/23 |

FOREIGN PATENT DOCUMENTS

| | | |
|---|---|---|
| JP | 8-256972 | 10/1996 |
| JP | 2000-139830 | 5/2000 |

* cited by examiner

*Primary Examiner* — Andrew Gilbert
(74) *Attorney, Agent, or Firm* — Ostrolenk Faber LLP

(57) ABSTRACT

A gas supply system appropriate for an abdominal cavity and a luminal cavity is provided. The gas supply system reduces a pressure of gas, supplied from a source of gas for supplying gas of a predetermined kind, to a predetermined pressure value upon which gas, whose pressure is reduced, is controllably lowered to a first pressure value appropriate for a body cavity of a first kind of a specimen to allow gas to be supplied to the body cavity of the first kind. In the meantime, gas, supplied from the source of gas, is lowered to a second pressure value appropriate for a body cavity of a second kind of the specimen to allow gas to be supplied to the body cavity of the second kind.

15 Claims, 12 Drawing Sheets

SYSTEM AND METHOD FOR SUPPLYING PREDETERMINED GAS AT TWO DIFFERENT PRESSURE VALUES

CROSS REFERENCE TO RELATED APPLICATIONS

The present application relates to and incorporates by reference to Japanese Patent Application No. 2004-100592 filed on Mar. 30, 2004, the entire content of which is hereby incorporated by reference.

BACKGROUND OF THE INVENTION

1. Technical Field

The present invention relates to a gas supply system and gas supply method for supplying gas to a body cavity of a patient to be operated, such as an abdominal cavity of a luminal cavity thereof, at two different predetermined pressure values.

2. Related Art

In recent years, laparoscopic surgeries have been practiced extensively. Under such laparoscopic surgeries, there are many probabilities where curative treatment is executed without opening an abdominal cavity for the purpose of treating a patient with minimally invasive capability.

Such laparoscopic surgeries have been executed in a way wherein a first trocar, through which, for instance, a rigidscope for observation is guided to a body cavity of the patient, and a second trocar, through which a treatment tool for executing curative treatment is guided to a site to be treated, are inserted to an abdominal portion of the patient.

Under such a laparoscopic surgery, with a view to ensuring a visual field of the rigidscope and ensuring an area for manipulating the treatment tool, an abdominal insufflation device has been used for supplying carbon dioxide gas (hereinafter also referred to as $CO_2$) as abdominal cavity gas to the abdominal cavity of the patient.

Further, various proposals have heretofore been undertaken in gas supply apparatuses such as an abdominal insufflation device that supplies carbon dioxide gas to the abdominal cavity.

For instance, Japanese Patent Provisional Publication No. 2000-139830 discloses a gas supply apparatus arranged to control a gas flow rate such that under situations where the gas flow rate is less than the set value, an electropneumatic proportional valve (or also referred to as an electromagnetic proportional valve), serving as a pressure regulator means, is supplied with a control signal to cause an outlet pressure to increase so as to allow an internal pressure of a living body to lie at the set value.

Further, Japanese Patent Provisional Publication No. 8-256972 discloses an abdominal insufflation device that has a structure in which a plurality of delivery conduit switching units (electromagnetic valves), which switches communicating states of gas delivery members extending from a gas supply source to an insertion tool for an abdominal cavity, are unitarily assembled with a manifold valve for thereby achieving a miniaturization of flow rate control units.

In the meanwhile, a luminal cavity, such as the stomach and large intestine or the like, has been diagnosed and treated using a flexiblescope, equipped with an elongated and flexible inserter adapted to be inserted into the luminal cavity, and a treatment tool, inserted through a forceps channel of the flexiblescope and protruding from a channel opening at a distal end of an inserted portion, for executing curative treatment.

When executing medical procedures, such as diagnosis and treatment of the luminal cavity such as the stomach and large intestine or the like, on the patient under observation with the endoscope, probabilities occur where the luminal cavity is supplied with gas, such as air as "luminal cavity gas", for the purpose of enhancing the visible field of the flexiblescope and enhancing the area for manipulating the treatment tool. Under such probabilities, although there are many cases where air, to be supplied to the luminal cavity, is delivered to the luminal cavity through the flexiblescope by a gas supply pump, it may be possible to use the above-described carbon dioxide gas.

Recently, new attempts have been undertaken where the laparoscopic surgeries are executed inserting a rigidscope to an abdominal cavity and inserting a flexiblescope to a luminal cavity while permitting both the endoscopes to be utilized for specifying a site for treatment. Even in such attempts, it has been probable that gas, such as air, for the luminal cavity is delivered to the luminal cavity through the flexiblescope inserted to the luminal cavity for distending the same.

However, in such cases, if air is delivered to the luminal cavity as described above, air is hard to be absorbed by the living body and, so, there are fears in that the luminal cavity remains under a distended state. For this reason, it has been contemplated to use an endoscope $CO_2$ regulator (hereinafter referred to as ECR) by which gas such as, for instance, carbon dioxide gas ($CO_2$) which can be easily absorbed by the living body, is supplied to the luminal cavity such as the large intestine or the like.

However, in cases where the related art endoscopic surgery system, for executing surgical operation under the endoscope, is structured to incorporate the ECR, the endoscopic surgery system needs a set of abdominal insufflation unit and a $CO_2$ container and a set of the ECR and the $CO_2$ container. This results in issues with the occurrence of troublesome preparation and inefficiency in space.

Further, abdominal cavity delivery gas and luminal cavity delivery gas differ in pressure from each other and, hence, carbon dioxide gas needs to be supplied to the abdominal cavity and luminal cavity at appropriate delivery pressures, respectively. Furthermore, since the ECR is designed to have a structure that is suitable for normal endoscopic inspection, that is, a structure in which carbon dioxide gas is supplied through the flexiblescope at a gas pressure suited only for the luminal cavity such as the large intestine, it becomes difficult sometimes for carbon dioxide gas to be adequately supplied because of an influence of an abdominal cavity pressure under the laparoscope.

SUMMARY OF THE INVENTION

The present invention has been completed with the above issues in mind and has an object to provide a gas supply system and supply method wherein gas can be supplied to an abdominal cavity and a luminal cavity of a patient to be operated at appropriate gas pressures, respectively.

In the present invention, the "luminal cavity" conceptually includes the stomach, a blood vessel, and the large intestine of a patient.

One aspect of the present invention provides a gas supply system comprising a source of gas adapted to supply gas of a predetermined kind, a first pressure regulator regulating the gas, supplied from the source of gas, to a first pressure value, and a second pressure regulator regulating the gas, supplied from the source of gas, to a second pressure value different from the first pressure valve.

Another aspect of the present invention provides a method of supplying gas, comprising reducing a pressure of gas, supplied from a source of gas from which the gas of a predetermined kind is supplied, to a predetermined value, reducing the pressure of the gas, whose pressure is reduced, to a first pressure value appropriate for a body cavity of a first kind of a specimen for supply to the body cavity of the first kind, while reducing the pressure of the gas, supplied from the source of gas, to a second pressure value appropriate for a body cavity of a second kind in the specimen for supply to the body cavity of the second kind.

According to another aspect of the invention, there is provided a gas supply system comprising a source of gas supplying gas of a predetermined kind, a first pressure reducing unit reducing the pressure of the gas, supplied from the source of gas, to a predetermined pressure, a first pressure regulator regulating the gas, whose pressure is reduced by the first pressure reducing unit to the predetermined pressure, to a first pressure value appropriate for a body cavity of a first kind in a specimen, a first flow rate regulator controlling a flow rate of the gas under the first pressure value regulated by the first pressure regulator, a first gas supply port, discharging the gas at a flow rate regulated by the first flow rate regulator, to which a delivering member connected to the body cavity of the first kind is connected, a second pressure reducing unit reducing the pressure of the gas, supplied from the source of gas, to a second pressure value appropriate for a body cavity of a second kind in the specimen, a second flow rate regulator controlling a flow rate of the gas under the second pressure value regulated by the second pressure regulator, and a second gas supply port, discharging the gas at a flow rate regulated by the second flow rate regulator, to which a delivering member connected to the body cavity of the second kind is connected.

According to a further aspect of the invention, there is provided a gas supply system for use in a laparoscopic surgery system that needs abdominal cavity gas supply under observation and treatment using a rigidscope and luminal cavity gas supply under observation and treatment using a flexiblescope, the gas supply system comprising a source of gas supplying gas of a predetermined kind, a first pressure regulator regulating the gas, supplied from the source of gas, to a first pressure value, and a second pressure regulator regulating the gas, supplied from the source of gas, to a second pressure value different from the first pressure valve.

With such a structure, gas can be supplied to the abdominal cavity and luminal cavity at gas supply pressures appropriate for these cavities, respectively.

DETAILED DESCRIPTION OF THE PREFERRED EMBODIMENTS

Now, various embodiments according to the present invention are described with reference to the accompanying drawings.

First Embodiment

Referring to FIGS. 1 to 6, a gas supply system of a first embodiment according to the present invention is described. Also, a gas supply method of the present invention is executed by such a gas supply system on functions thereof.

Figure 1:
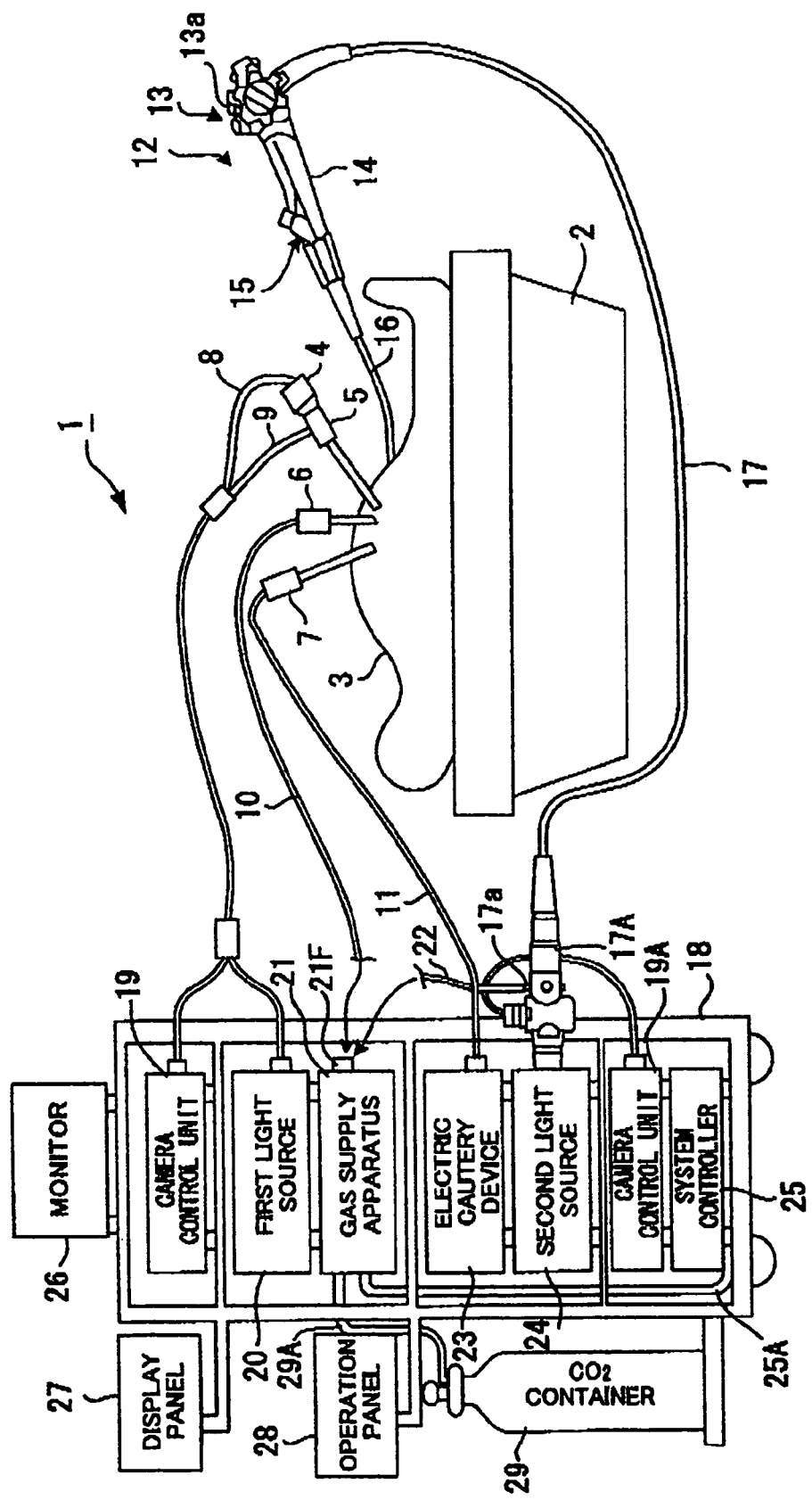
FIG. 1 is an overall structural view of an endoscopic surgical operation system equipped with a gas supply apparatus of a first embodiment according to the present invention.

FIG. 1 shows a schematic structure of an endoscopic surgical operation system 1. The gas supply system GSS of the presently embodiment is unitarily incorporated in the endoscopic surgical operation system 1. The gas supply system GSS is described herein in conjunction with the endoscopic surgical operation system 1. The relationship between the gas supply system GSS and the endoscopic surgical operation system 1 similarly applies to second and third embodiments that will be described below.

As shown in FIG. 1, the endoscopic surgical operation system 1 is comprised of a rigidscope 5, carrying thereon a TV camera head 4 incorporating therein an image pickup device, which is inserted through a trocar (not shown) to and placed in an abdominal cavity of a patient 3 who lies down on an operation table 2. With a view to enhancing an observation visible field for the rigidscope 5, the endoscopic surgical operation system 1 is further comprised of an abdominal insufflation guide tube 6, through which carbon dioxide gas is supplied to an inside of the abdominal cavity of the patient 3 for abdominal insufflation, and an electric cautery probe 7, connected to an electric cautery device 23, for executing electrical cautery treatment on an affected site. To this end, the abdominal insufflation guide tube 6 and the electric cautery probe 7 are inserted to and placed in the patient 3.

Connected to the TV camera head 4 is a signal cable 8. Connected to the rigidscope 5 is a light guide cable 9. Also, connected to the abdominal insufflation guide tube (trocar) 6 is an abdominal insufflation tube (hereinafter referred to as an abdominal cavity tube) 10. Moreover, connected to the electric cautery probe 7 is a signal cable 11.

The signal cable 8 and light guide cable 9 are connected to a TV camera device (camera control unit that will be hereinafter referred to as a CCU) 19 and a first light source 20, which are mounted on a trolley 18. The abdominal cavity tube 10 is connected to a gas supply apparatus 21, serving as an abdominal insufflation device, which is mounted on the trolley 18. Moreover, the signal cable 11 is connected to the electric cautery device 23 mounted on the trolley 18.

Further, the endoscopic surgical operation system 1 of the presently filed embodiment is comprised of a flexiblescope 12 for performing endoscopic inspection of an internal part of a luminal cavity, such as the large intestine, of the patient 3. The flexiblescope 12 is configured such that upon depressing a gas supply button 13a, carbon dioxide gas, delivered from the gas supply apparatus 21, can be delivered from a distal end of an inserter 16 via a delivery conduit (not shown) disposed inside a universal chord 17.

The gas supply button 13a is located on a rear end of a manipulator 13 that doubles as a gripper 14. Also, the gas supply button 13a is formed with an open aperture (not shown) through which supply gas is adapted to be released. An operator is enabled to block the open aperture with a finger to allow gas to be delivered to the luminal cavity.

The universal chord 17 is internally provided with a signal cable, a light guide and the gas supply conduit, although not shown. The universal chord 17 is connected via a connector 17A to a second light source 24 mounted on the trolley 18.

The connector 17A has a carbon dioxide supply port 17a, to which a luminal cavity tube 22 is connected, through which carbon dioxide gas is supplied from the gas supply apparatus 21.

Moreover, the abdominal cavity tube 10 and the luminal cavity tube 22 are selectively connected to the gas supply apparatus 21 in a manner as described below.

Mounted on the trolley 18 is the CCU 19 in which signal processing is carried out for the image pickup device, the first light source 20 from which an illumination light is supplied to the rigidscope 5, the gas supply apparatus 21 from which gas (carbon dioxide gas) is supplied to the abdominal cavity and luminal cavity, the electric cautery device 23 from which electric power is supplied to the electric cautery probe at a high output frequency for cautery, and the second light source 24 from which an illumination light is supplied to the flexiblescope 12.

Further, mounted on the trolley 18 are a system controller 25, which performs control of the whole system, a CCU 19A for executing signal processing for the image pickup device contained in the flexiblescope 12, a VTR (not shown) that registers image signals from the CCUs 19, 19A, a monitor 26 on which the image signals from the CCUs 19, 19A are displayed in images, and a carbon monoxide container (CO2 steel bottle) 29 that supplies carbon dioxide under pressure to the gas supply apparatus 21 via a high-pressure tube 29A.

Further, a display panel 27 for providing a display and an operation panel 28 through which operation is executed are disposed on the trolley 18.

Further, functionally provided in the system controller 25 are an operation signal receiver section receiving signals from an operation panel 28 and a setting and operator unit 41 (see FIG. 4) of the gas supply apparatus 21 that will be described later, an information generating section generating information required for display on the display panel 27 and the display unit 42 of the gas supply apparatus 21 based on received signals, and a display transmitter section transmitting this information to the display panel 27 and display unit 42 of the gas supply apparatus 41 for display. With the presently filed embodiment, the system controller 25 is comprised of a computer including a CPU that operates based on programs preliminarily stored in internally contained memories to execute operations on software to allow the operation signal receiver section, the information generating section and display transmitter section to exhibits respective functions.

As apparent from the structure set forth above, the gas supply system GSS of the presently filed embodiment is comprised of principal components such as the carbon dioxide gas container (CO2 steel bottle) 29, the high-pressure gas tube 29A, the gas supply apparatus 21, the abdominal cavity tube 10, the luminal cavity tube 22, the system controller 25, the display panel 27 and the operation panel 28.

Further, the system controller 25 electrically connected to a communication unit (not shown) that communicates with medical equipment mounted on the trolley 18. The communication unit (not shown) is connected to the CCUs 19, 19A, the first light source 20, the gas supply apparatus 21, the electric cautery device 23, the second light source 24 and the VTR (not shown) via communication cables, enabling these medical equipment to achieve bidirectional communication with the communication unit.

The system controller 25 also internally includes an image signal processing section (not shown). The image signal processing section (not shown) is configured in structure to enable image information, resulting from image signals delivered from the CCUs 19, 19A, to be transmitted to the monitor 26.

Figure 2:
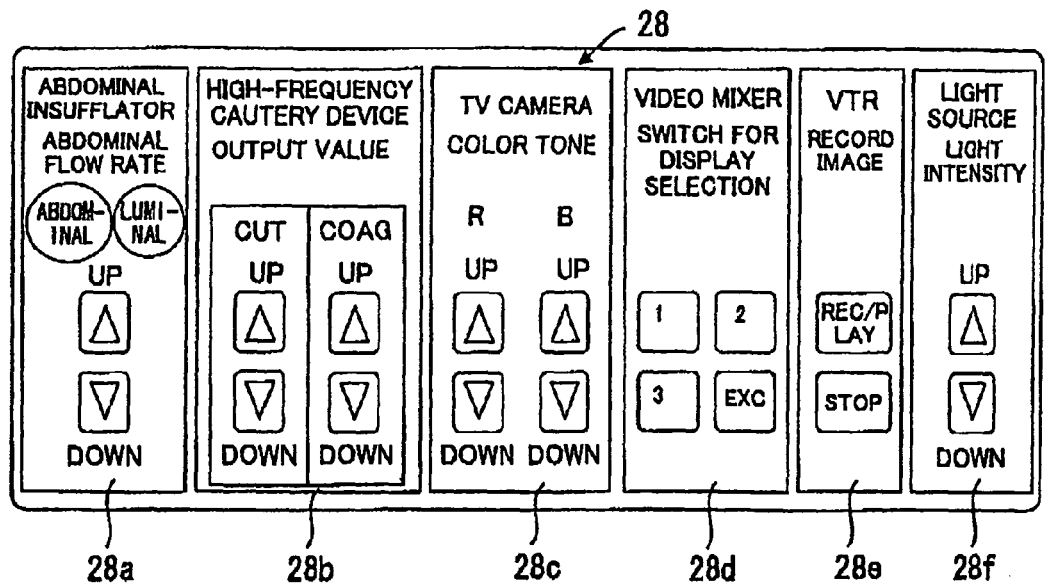
FIG. 2 is an image structural view illustrating an operation panel shown in FIG. 1.

An exemplary structure of the operation panel 28, shown in FIG. 1, is illustrated in FIG. 2.

As shown in FIG. 2, the operation panel 28 is comprised of setting and operating buttons 28a for adjusting the flow rate of carbon dioxide gas, to be supplied to the abdominal cavity or luminal cavity from the gas supply apparatus (serving as an abdominal insufflation device) 21, operating buttons 28b through which an output value of the electric cautery device (high frequency combustion device) 23 is adjusted, operating buttons 28c that enable the adjustment of color tones of the first and second CCUs (TV camera) 19 and 19A, operating buttons 28d commanding a display to be switched over between a first image (an endoscope image resulting from the rigidscope) and a second image (an endoscope image resulting from the flexiblescope) for display over the monitor 26, operating buttons 28e commanding to start or stop recording information on the VTR, and operating buttons 28f through which light intensities of the first and second light sources 20 and 24 are adjusted.

Figure 3:
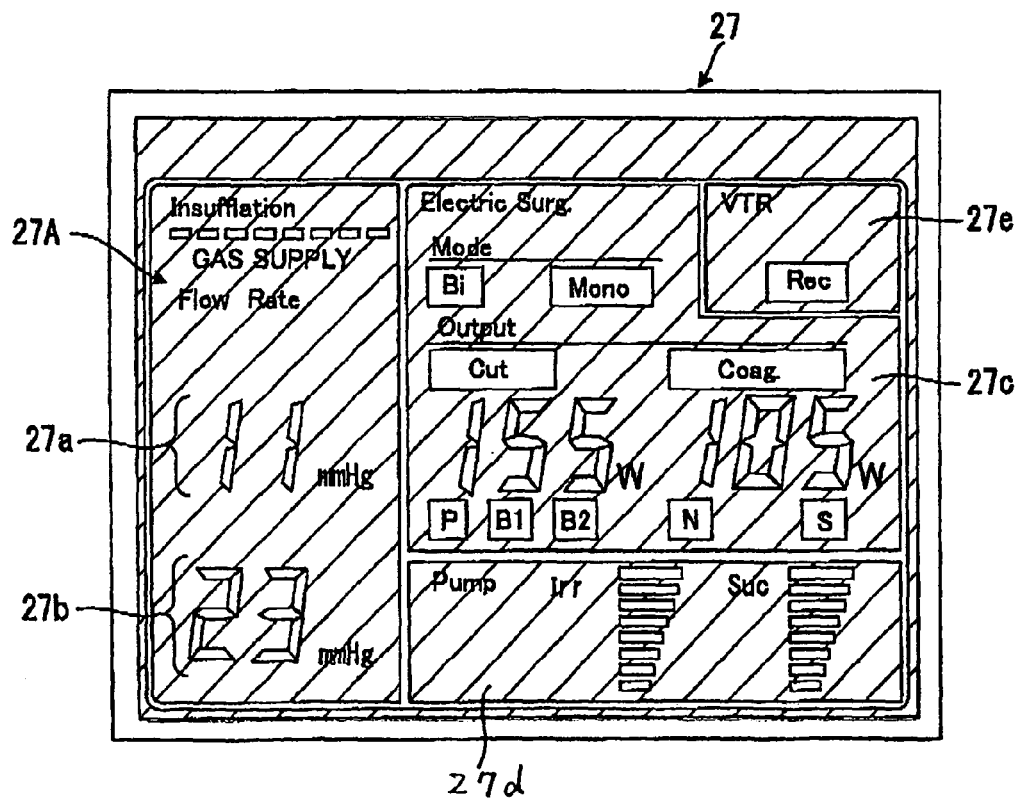
FIG. 3 is an image structural view illustrating an operation panel shown in FIG. 1.

One example of a display screen of the display panel 27, shown in FIG. 1, is illustrated in FIG. 3.

As shown in FIG. 3, provided on the display screen of the display panel 27 are display areas 27A, (27a, 27b), 27c, 27d and 27e that are configured to display the setting and operating conditions related to functions of the gas supply apparatus 21, the electric cautery device 23, the water supply and suction pumps (not shown) and the VTR, respectively, which are controlled by the system controller 25 on radio communication. Also, the display areas 27A is configured to provide displays of setting and operating states of the gas supply apparatus 21 and includes a display 27a of an amount of gas to be delivered into the luminal cavity, a display 27c of an abdominal-cavity internal-pressure preset value, a display for a remaining volume of carbon dioxide gas, and a display of the flow rate of carbon dioxide gas.

Figure 4:
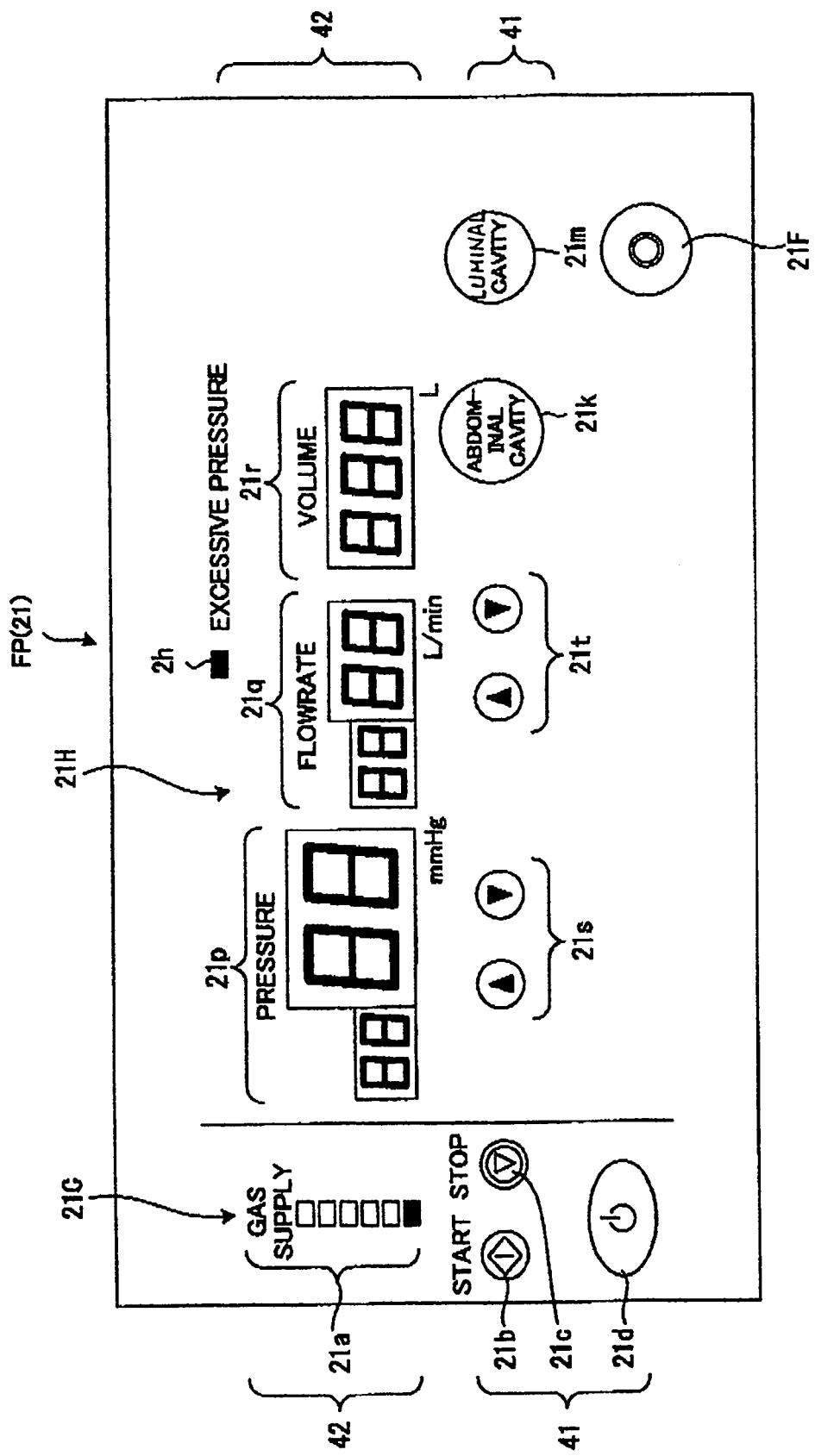
FIG. 4 is a structural view showing a setting and operating unit and a display section of the gas supply apparatus shown in FIG. 1.

With reference to FIG. 4, structural examples of the setting and operating unit 41 and display unit 42, both serving as a commanding device, which are provided on a front panel FP of the gas display apparatus 21 will now be described.

As shown in FIG. 4, provided on the front panel FP formed on the gas supply apparatus 21 at one side thereof, respectively, are the setting and operating unit 41 and the display unit 42, which have been described above. The setting and operating unit 41 and display unit 42 are divided in, for instance, a supply source setting and display section 21C for achieving the setting, operating and displaying on various parameters related to the carbon dioxide container 29, and a setting and display section 21H for achieving the setting, operating and displaying on various parameters related to the abdominal cavity and luminal cavity.

Provided below the setting and display section 21H is a supply fitting 21F that serves as a gas supply port to which the abdominal cavity tube 10 or the luminal cavity tube 22 are selectively connected. Such a layout structure allows the operator to easily manipulate and various displays to be easily viewable.

Provided in the supply source setting and display section 21C are a gas remaining volume display portion 21a, a gas-delivery start button 21b and gas-delivery stop button 21c, and a power switch 21d.

In the setting and display section 21H, there are provided a pressure display portion 21p, a flow rate display portion 21q, a delivery-gas remaining volume display portion 21r and a gas pressure alarm lamp 2h, all of which serve as the display unit 42, pressure setting buttons 21s, delivery gas flow-rate setting buttons 21t, an abdominal cavity command button 21k and a luminal cavity command button 21m, all of which serve as the setting and operating unit 41.

The pressure setting buttons 21s and delivery gas flow-rate setting buttons 21t includes two operation buttons for incrementing and decrementing associated parameters, respectively, which can be suitably operated in directions to gradually increment or decrement preset values.

The delivery-gas remaining volume display portion 21r is configured to provide a display of a residual volume of carbon dioxide gas remaining in the carbon dioxide gas container 29. The gas-delivery start button 21b serves as a button that commands starting to supply gas. The gas-delivery stop button 21c serves as a switch that switches from a gas delivery state to a gas-delivery stop state. The power switch 21d serves as a switch that switches a power supply of the gas supply apparatus between a turn-on state and turn-off state.

The pressure display portion 21p includes two display areas on left and right sides, with the right display area providing a display of a value indicative of a measured value of the pressure sensor 37 while the left display area provides a display of a preset pressure that is preset upon operation of, for instance, the pressure setting buttons 21s.

The flow rate display portion 21q includes two display areas on left and right sides, with the right display area providing a display of a value indicative of a measured value of the flow rate sensor 38 while the left display area provides a display of a preset flow rate that is preset upon operation of, for instance, the gas delivery flow rate setting buttons 21t.

The delivery-gas remaining volume display portion 21r is configured to provide a display of a delivery gas total volume required upon calculation in a controller 40 based on the measured value of the flow rate sensor 38.

The gas pressure alarm lamp 2h is configured to shift from a turnoff state to a flashing display state or red glow state in response to a control signal delivered from the controller 40, when the measured value of the pressure sensor 37 exceeds the pressure set value by a predetermined level, for thereby providing the operator with notification of the abdominal cavity or luminal cavity internal pressures exceeding the associated preset pressure values.

A structure of the gas supply apparatus 21 will now be described below with reference to FIG. 5.

Figure 5:
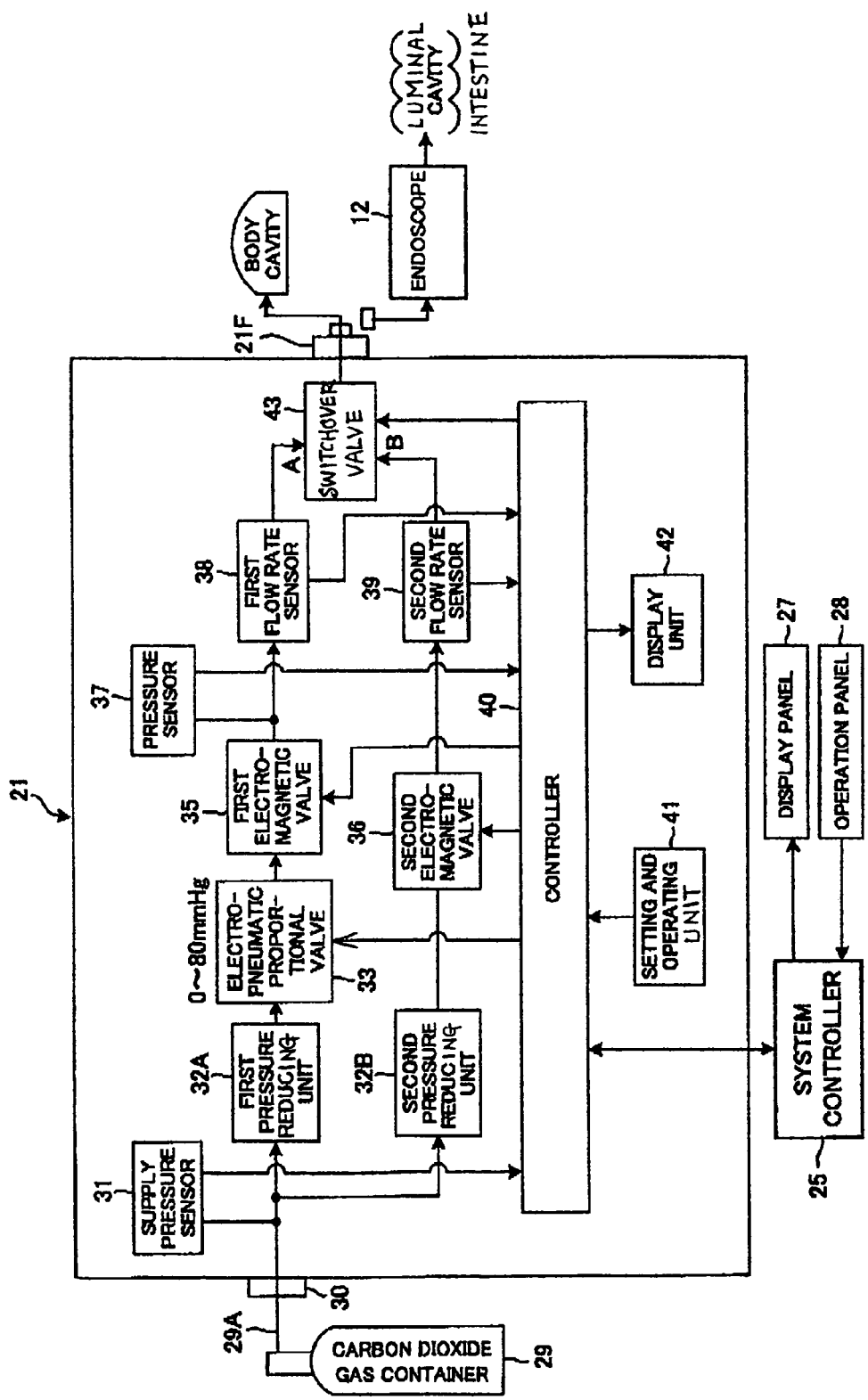
FIG. 5 is a block diagram for illustrating a structure of the gas supply apparatus shown in FIG. 1.

As shown in FIG. 5, the gas supply apparatus 21 is comprised of a high pressure fitting 30, a supply pressure sensor 31, a first pressure reducing unit 32A and electropneumatic proportional valve 33 serving as a first pressure regulator means, a second pressure reducing unit 32B serving as a second pressure regulator means, first and second electromagnetic valves 35, 36 serving as opening and closing valves, respectively, for opening and closing associated flow channels, a pressure sensor 37 serving as a delivery gas pressure measuring unit, first and second flow rate sensors 38, 39 serving as flow rate measuring units, a switchover valve 43 serving as a switching member, the controller 40, the setting and operating unit 41, the display unit 42 and the supply fitting 21F.

The electropneumatic proportional valve 33 is also structured of an electromagnet, formed of a magnet coil and magnet needle that are not shown, which is electrically operative to adjust a pressure reducing spring acting on a pressure control thin film for thereby variably regulating a pressure in a downstream in proportion to an input voltage (current).

Connected between the carbon dioxide gas container 29 and the gas supply apparatus 21 is the high-pressure gas tube 29A, which has one end adapted for connection to the high-pressure fitting 30 provided in the gas supply apparatus 21.

Extending form the system controller 25 is a signal cable 25A detachably mounted to an electrical connector (not shown) of the gas supply apparatus 21 for electrical connection to the controller 40 internally located in the gas supply apparatus 21.

The other end (connector portion) of the abdominal cavity tube 10 and other end (connector portion) of the luminal cavity tube 22 are selectively and detachably connected to the supply fitting 21F mounted in the gas supply apparatus 21.

With a cock of the carbon dioxide gas container 29 being opened, carbon dioxide gas, stored in the carbon dioxide gas container 29 in a liquid form, is vaporized to form carbon dioxide gas that is delivered to internal delivering members formed in two lies for the abdominal cavity and luminal cavity via internal delivering members disposed inside the gas supply apparatus 21.

Carbon dioxide gas, introduced to the delivering member for the abdominal cavity, is reduced in pressure to a given pressure by the first pressure reducing unit 32A and, then, further regulated in pressure by the electropneumatic proportional valve 33 to a pressure appropriate for supply to an inside of the abdominal cavity upon which carbon dioxide gas is delivered to the switchover valve 43 via the first electromagnetic valve 35 and first flow rate sensor 38. Here, when the abdominal cavity command button 21k is depressed to select an abdominal cavity gas delivery mode, the switchover valve 43 is switched to an inlet A to allow carbon dioxide gas to flow to the supply fitting 21F. Under situations where the abdominal cavity tube 10 is selectively connected to the supply fitting 21F, carbon dioxide gas is introduced to the inside of the abdominal cavity through the abdominal cavity tube 10 and flow channel (delivering member: not shown) disposed in the abdominal cavity guide tube 6.

In the meanwhile, carbon dioxide gas, introduced to the delivering member for the luminal cavity, is reduced in pressure by the second pressure reducing unit 32B to a pressure appropriate for supply to an inside of the luminal cavity and delivered to the switchover valve 43 via the second electromagnetic valve 35 and second flow rate sensor 39. Here, when the luminal cavity command button 21m is depressed for selection of a luminal cavity gas delivery mode, the switchover valve 43 is switched to an inlet B to allow carbon dioxide gas to flow to the supply fitting 21F. Under situations where the luminal cavity tube 22 is selectively connected to the supply fitting 21F, carbon dioxide gas is supplied to the flexiblescope 12 through the luminal cavity tube 22, the connector portion 17A and the universal chord 17.

The supply pressure sensor 31 measures the pressure of carbon dioxide gas flowing from the carbon dioxide gas container 29 to allow the measured result to be outputted to the controller 40. The detection signal resulting from the supply pressure sensor 31 is used for display carried out by the gas remaining volume display portion 21*a*.

The first pressure reducing unit 32A reduces the pressure of carbon dioxide gas, supplied from the carbon dioxide gas container 29, to a predetermined pressure, upon which carbon dioxide gas is supplied to the electropneumatic proportional valve 33.

The electropneumatic proportional valve 33 is enabled to control the pressure of carbon dioxide gas and further reduce the pressure of carbon dioxide gas, whose pressure is already reduced by the first pressure reducing unit 32A, to a predetermined gas delivery pressure, in the order of 0 to 80 mmHg appropriate for the abdominal cavity, in response to the control signal from the controller 40.

In the meanwhile, the second pressure reducing unit 32B reduces the pressure of carbon dioxide gas, supplied from the carbon dioxide gas container 29, to another predetermined gas delivery pressure in a range of approximately 100 to 500 mmHg appropriate for the luminal cavity.

The first and second electromagnetic valves 35, 36 serve as the valves, each of which is controllably opened or closed by the controller 40 and switched over between a closed and open state depending on a control signal from the controller 40.

The pressure sensor 37 serves to measure a pressure inside the abdominal cavity with the first electromagnetic valve 35 being closed, thereby outputting the resulting measured value to the controller 40.

The first flow rate sensor 38 serves to measure the flow rate of carbon dioxide gas passing across the first electromagnetic valve 35 and flowing through the associated internal delivering member, upon which the resulting measured result is outputted to the controller 40. The second flow rate sensor 39 serves to measure the flow rate of carbon dioxide gas passing across the second electromagnetic valve 36 and flowing through the associated internal delivering member, upon which the resulting measured result is outputted to the controller 40.

Further, although not shown in the drawing figure, an exhaust valve (not shown) may be connected between the first electromagnetic valve 35 and first flow rate sensor 38. In such a case, the exhaust valve is configured to assume an open state to reduce a pressure inside the abdominal cavity in response to a control signal from the controller 40 under cases where the measured value of the pressure sensor 37 exceeds an abdominal cavity internal pressure set value. Thus, the gas supply apparatus 21 is enabled to release carbon dioxide gas to the atmosphere from the abdominal cavity.

With the presently filed embodiment, the controller 40 is comprised of a computer incorporating a CPU (Central Processing Unit)), not shown, and memory devices such as ROM and RAM, and the CPU is configured to exhibit various functions upon executing given calculations in accordance with programs preliminarily stored in the ROM. These various functions may include various controls, such as pressure control for the electropneumatic proportional valve 33 depending on the detected result of the pressure sensor 37, opening and closing controls for the first and second electromagnetic valves 35, 36 depending on the detected results of the first and second flow rate sensors 38, 39, display control for the display unit 42, gas delivery start and gas delivery stop controls in response to operation signals inputted by the setting and operating unit 41, and controls for alteration of the pressures, alteration of the flow rates and selecting abdominal cavity and luminal cavity modes. Controls, to be executed in response to operations, may include switching control for switching internal flow channels in the switchover valve 43.

Of course, the controller 40 is configured to communicate with the system controller 25 to, in an independent or cooperative manner, accomplish various kinds of control necessary in the system.

Also, the controller 40 may not be limited to a structure that is necessarily comprised of the computer and an alternative may include a digital circuitry or analog circuitry composed of various logic circuits.

Description will now be made of a basic sequence of operations of the gas supply system GSS of the presently filed embodiment.

It is supposed that when carrying out laparoscopic surgery employing the endoscopic surgical operation system 1, an operator inserts the rigidscope 5 into the inside of the abdominal cavity while inserting the flexiblescope 12 into the luminal cavity, such as the large intestine, to specify a site to be treated for curative treatment.

Upon operation of the operator to depress the abdominal cavity command button 21*k* and gas-delivery start button 21*b*, the controller 40 regulates the electropneumatic proportional valve 33 to achieve abdominal cavity pressure control such that the supply fitting 21F, to which the abdominal cavity tube 20 is connected, is supplied with carbon dioxide gas regulated to pressure appropriate for the abdominal cavity in a manner described above.

As used herein, the term "abdominal cavity pressure control" refers to control that is executed to controllably vary an opening degree of the electropneumatic proportional valve 33, depending on the measured result of the pressure sensor 37 while opening and closing the first electromagnetic valve 35, such that a pressure inside the abdominal cavity is maintained in a preset value. That is, the abdominal cavity pressure control is repeatedly executed in a manner wherein under a condition where the first electromagnetic valve 35 is closed to shut off the supply of carbon dioxide gas, the pressure inside the abdominal cavity is measured by the pressure sensor 37 that provides the measured result based on which the opening degree of the electropneumatic proportional valve 33 is controlled to maintain the pressure inside the abdominal cavity in the preset value.

Upon operation of the operator to operate the luminal cavity command button 21*m* and gas-delivery start button 21*b*, the supply fitting 21F, to which the luminal cavity tube 22 is connected, is supplied with carbon dioxide gas under pressure regulated to a value appropriate for the luminal cavity in a manner described above.

Before executing the operation, the cock of the carbon dioxide gas container 29 is preliminarily opened in a manner as described above to supply carbon dioxide gas under a high pressure to the gas supply apparatus 21 upon which carbon dioxide gas is introduced through the internal delivering member to the internal delivering members formed in the two lines for the abdominal cavity and luminal cavity.

As set forth above, carbon dioxide gas introduced to the delivering member for the abdominal cavity is reduced in pressure to a predetermined level by the first pressure reducing unit 32A and then further regulated by the electropneumatic proportional valve 33 to a pressure appropriate for supply to the abdominal cavity, upon which carbon dioxide gas is delivered to the switchover valve 43 through the first electromagnetic valve 35 and first flow rate sensor 38.

In the meanwhile, carbon dioxide gas introduced to the delivering member for the luminal cavity is reduced in pressure by the second pressure reducing unit 32B to a pressure appropriate for supply to the luminal cavity, upon which carbon dioxide gas is delivered to the switchover valve 43 through the second electromagnetic valve 36 and second flow rate sensor 39.

Figure 6:
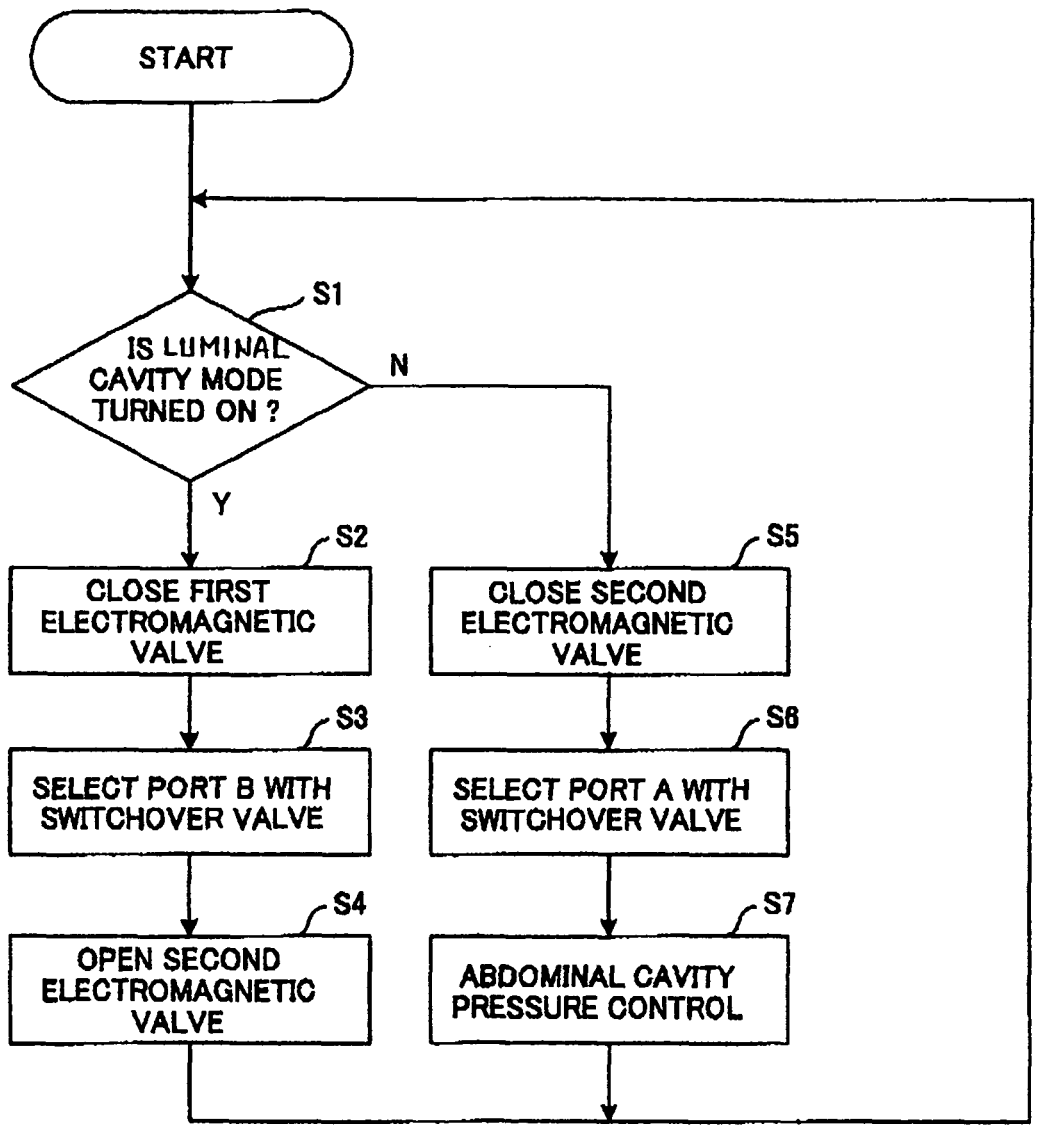
FIG. 6 is a flowchart showing exemplary control operations of a controller shown in FIG. 5.

Operations of the gas supply system GSS of the presently filed embodiment are described further in detail with reference to a flow chart of FIG. 6.

It is now assumed that the luminal cavity tube 22 is connected to the supply fitting 21F and the luminal cavity command button 21m is depressed to turn on a luminal cavity gas delivery mode in the gas supply apparatus 21.

Initially, the controller 40 discriminates whether or not the luminal cavity gas delivery mode is turned on with the luminal cavity command button 21m being operated (step S1). With the luminal cavity gas delivery mode turned on, the controller 40 enters the luminal cavity gas delivery mode. The controller 40 closes the first electromagnetic valve 35 (step S2) and switches the switchover valve 43 to the port B (step S3) while opening the second electromagnetic valve 36 (step S4).

Since the first electromagnetic valve 35 is closed, no carbon dioxide gas is supplied to the delivering member for the abdominal cavity. Accordingly, carbon dioxide gas is supplied from the second pressure reducing unit 32B to the inside of the luminal cavity through the second electromagnetic valve 36, the second flow rate sensor 39, the supply fitting 21F, the luminal cavity tube 22, the connector portion 17A, the universal chord 17 and the flow channel (delivering member: not shown) provided in the flexiblescope 12.

This allows the gas supply apparatus 21 to supply carbon dioxide gas under pressure regulated to a value appropriate for the luminal cavity, that is, a value of approximately 100 to 500 mmHg.

In contrast, it is assumed that the abdominal cavity tube 10 is connected to the supply fitting 21F and the abdominal cavity command button 21k is operated to turn on an abdominal cavity gas delivery mode in the gas supply apparatus 21.

With the abdominal cavity gas delivery mode turned on, the controller 40 enters the abdominal cavity gas delivery mode. The controller 40 closes the second electromagnetic valve 36 (step S5) and switches the switchover valve 43 to the port A (step S6) while performing abdominal cavity pressure control (step S7).

Carbon dioxide gas, whose pressure is reduced to a predetermined pressure by the first pressure reducing unit 32A, is further regulated to a pressure and gas delivery flow rate appropriate for the abdominal cavity by the electropneumatic proportional valve 33 controlled in response to a control signal delivered from the controller 40.

Since the second electromagnetic valve 36 is closed, no carbon dioxide gas is supplied to the delivering member for the luminal cavity. Accordingly, carbon dioxide gas is introduced to the delivering member for the abdominal cavity and supplied to the abdominal cavity through the first electromagnetic valve 35, the first flow rate sensor 38, the supply fitting 21F, the abdominal cavity tube 10 and the flow channel (delivering member: not shown) provided in the abdominal cavity guide tube 6.

When this takes place, the first flow rate sensor 38 measures the flow rate of carbon dioxide gas passing across the first electromagnetic valve 35 and flowing through the internal delivering member and the reassured result is outputted to the controller 40. Further, the pressure sensor 37 measures the pressure inside the abdominal cavity when the first electromagnetic valve 35 is closed, thereby outputting the measured result to the controller 40.

Therefore, the controller 40 is responsive to the measured results delivered from the first flow rate sensor 38 and the pressure sensor 37 to control the electropneumatic proportional valve 33 and first electromagnetic valve 35 so as to perform abdominal cavity pressure control such that carbon dioxide gas, to be supplied to the abdominal cavity, is regulated to a gas delivery pressure in the range of 0 to 80 mmHg and flow rate in the range of 0.1 to 35 L/min appropriate for supplying carbon dioxide gas to the abdominal cavity. Also, after performing abdominal cavity pressure control, the controller 40 allows the operation to return to step S1 and repeatedly execute the operations in steps S1 to S4 or step S7 until the supply of carbon dioxide gas is completed.

Thus, the gas supply apparatus 21 of the presently filed embodiment operates in such a manner that the controller 40 controls the electropneumatic proportional valve 33 to perform abdominal cavity pressure control to allow carbon dioxide gas to be supplied to the abdominal cavity under the pressure suited thereto.

Accordingly, with the presently filed embodiment, a single gas supply apparatus 21 can be configured to have a function of an abdominal insufflation device and a function of the ECR with capabilities for delivering carbon dioxide gas both to the abdominal cavity and luminal cavity under respective appropriate pressures, enabling the provision of a structure that is small in size and low in costs.

Second Embodiment

A gas supply system of a second embodiment according to the present invention is described with reference to FIGS. 7 to 10.

The gas supply apparatus of the second embodiment features supplying carbon dioxide gas to both the abdominal cavity and luminal cavity at the same time. That is, although the first embodiment, set forth above, takes the form of a structure in which the abdominal cavity tube 10 and luminal cavity tube 22 are selectively switched for supply of carbon dioxide gas to the abdominal cavity and luminal cavity, the second embodiment is structured such that both the abdominal cavity tube 10 and luminal cavity tube 22 are simultaneously connected to supply carbon dioxide gas to the abdominal cavity and luminal cavity in a concurrent fashion. Other structures are similar to those of the first embodiment and the same component parts bear like components to omit or simplify description. The way of such omission or simplification in description is similarly applied to a third embodiment described below.

Figure 7:
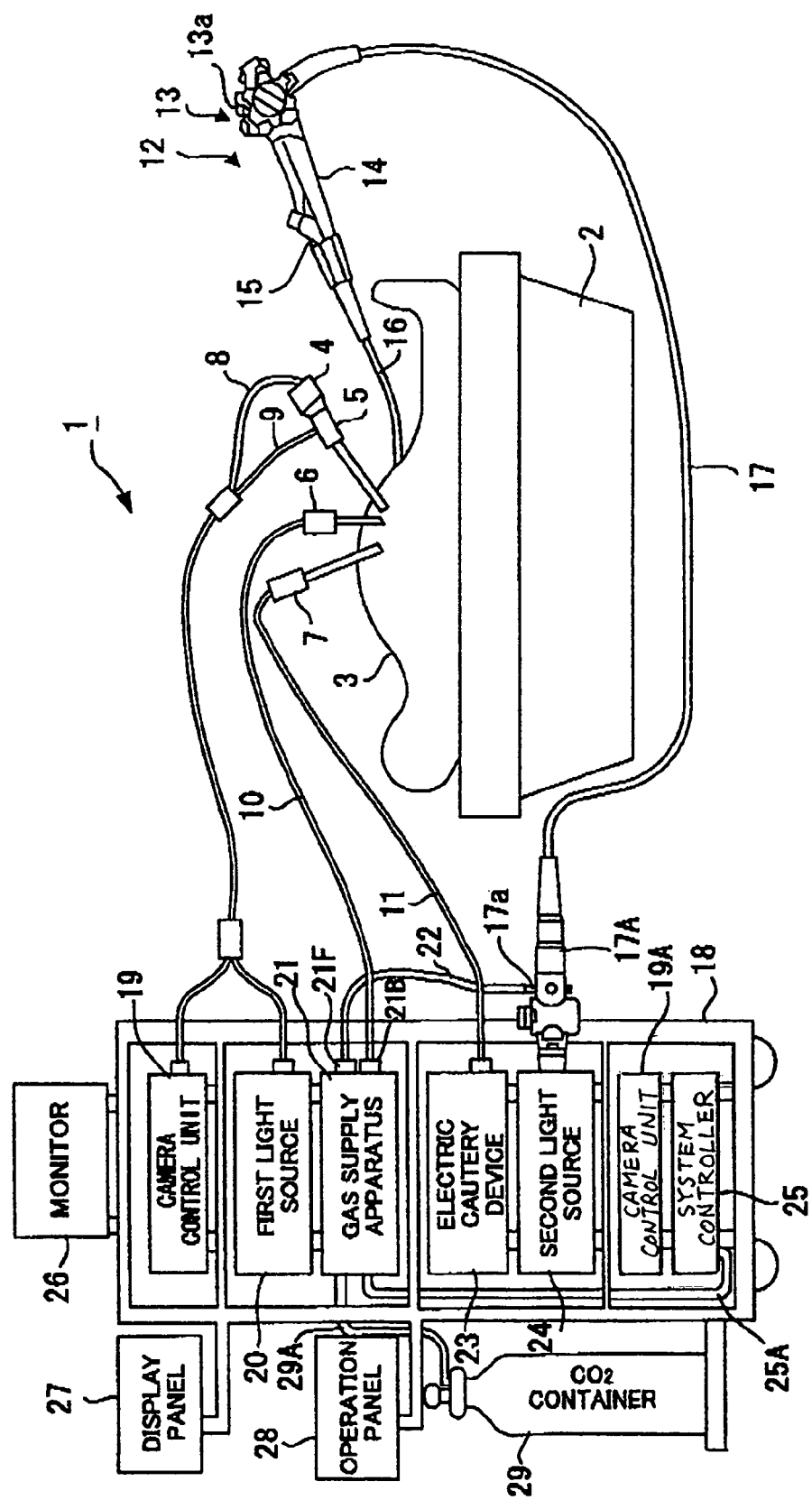
FIG. 7 is an overall structural view of an endoscopic surgical operation system equipped with a gas supply apparatus of a second embodiment.

As shown in FIG. 7, the gas supply apparatus 45 is structured such that both the abdominal cavity tube 10 and luminal cavity tube 22 are simultaneously connected.

Figure 8:
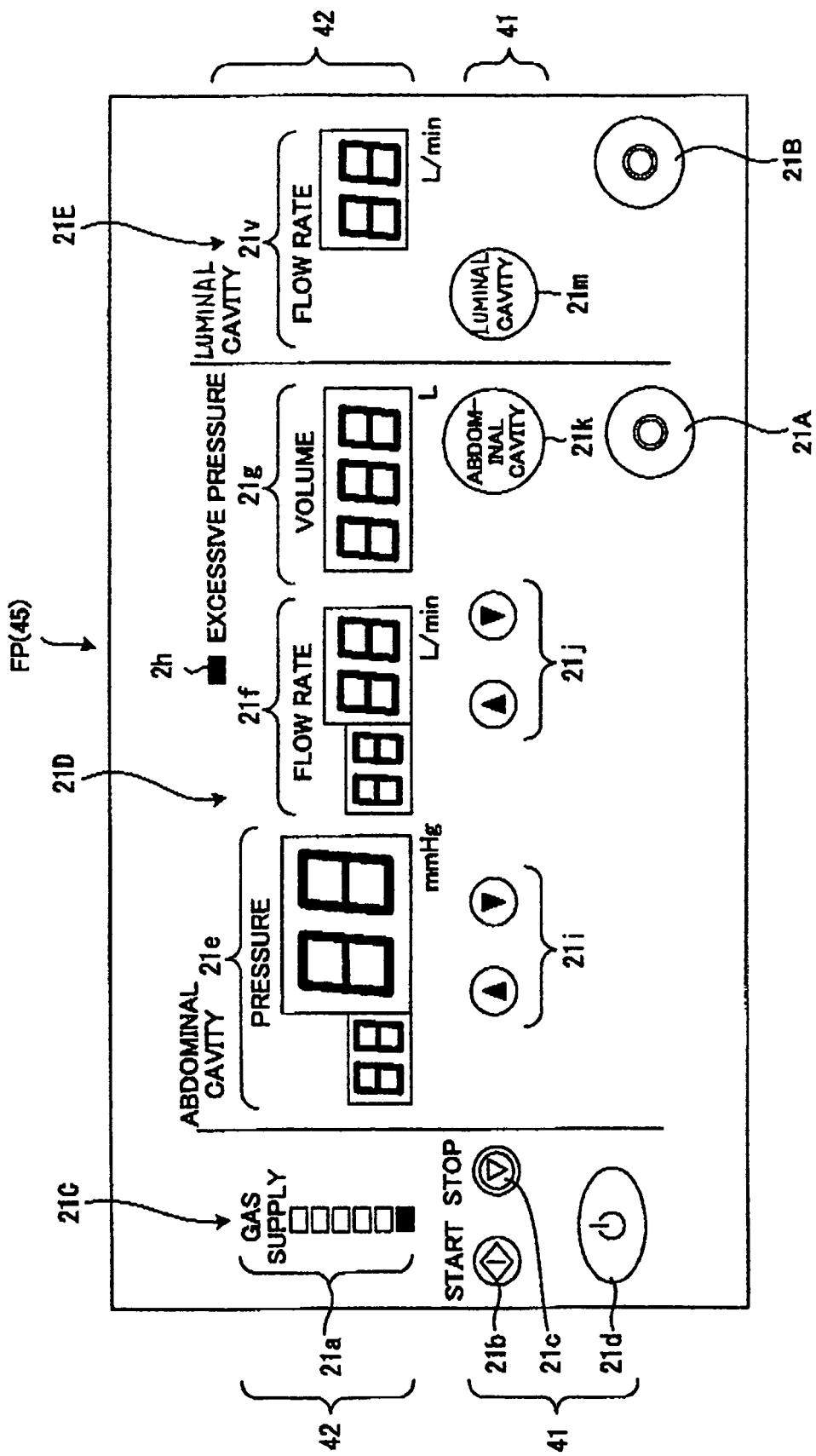
FIG. 8 is a view showing schematic structures of a setting and operating unit and display section of the gas supply apparatus shown in FIG. 7.

In addition, as shown in FIG. 8, disposed on a front panel FP of the gas supply apparatus 45 are the setting and operating unit 41 and the display unit 42. The setting and operating unit 41 and display unit 42 are divided into the supply source setting and display section 21C, an abdominal cavity setting and display section 21D for setting, operating and displaying parameters for the abdominal cavity, and a luminal cavity setting and display section 21E for setting, operating and displaying parameters for the luminal cavity. Further, disposed below the abdominal cavity setting and display section 21D is an abdominal cavity supply fitting 21A serving as an abdominal cavity gas supply port. In addition, disposed below the luminal cavity setting and display section 21E is a luminal cavity supply fitting 21B serving as a luminal cavity gas supply port. Such a layout structure allows the operator to easily operate the gas supply apparatus 45, permitting the respective displays to be easily viewable.

Disposed in the abdominal cavity setting and display section 21D are an abdominal cavity internal pressure display portion 21e, an abdominal-cavity flow rate display portion 21f, an abdominal-cavity delivery-gas total volume display portion 21g and a gas pressure alarm lamp 2h, abdominal body internal pressure setting buttons 21i forming the setting and operating unit 41, abdominal cavity delivery gas flow rate setting buttons 21j, and an abdominal cavity command button 21k.

Provided in the luminal cavity setting and display area 21E is a luminal cavity flow rate display portion 21v and a luminal cavity command button 21m.

The abdominal cavity internal pressure setting buttons 21i and the abdominal cavity delivery gas flow rate setting buttons 21j includes operation buttons for incrementing or decrementing parameters, respectively, which are configured such that suitably operating these buttons in modes for incrementing or decrementing associated parameters allows preset values to increase or decrease.

The abdominal cavity internal pressure display portion 21e includes two display areas on left and right sides with the right display area providing a display of a value indicative of a measured value of the pressure sensor 37 while the left display area provides a display of a preset pressure that is preset upon operation of, for instance, the pressure setting buttons 21i.

The abdominal cavity flow rate display portion 21f includes two display areas on left and right sides with the right display area providing a display of a value indicative of a measured value of the flow rate sensor 38 while the left display area provides a display of a preset flow rate that is preset upon operation of, for instance, the abdominal cavity gas delivery flow rate setting buttons 21j.

The abdominal cavity delivery gas total volume display portion 21g is configured to provide a display of a delivery gas total volume required upon calculation in a controller 40A based on the measured value of the flow rate sensor 38.

The gas pressure alarm lamp 2h is configured to shift from a turnoff state to flashing display state or red glow state for thereby providing the operator with notification of the pressure in the abdominal cavity exceeding the preset value in response to a control signal from the controller 40a when the measured value of the pressure sensor 37 exceeds the preset value for the internal pressure of the abdominal cavity by a predetermined value.

The abdominal cavity command button 21k plays a role as a button, by which the gas supply apparatus 45 is commanded to commence supplying carbon dioxide gas to the abdominal cavity, that is, a button for selecting the abdominal-cavity gas delivery mode.

In the meanwhile, the luminal cavity flow rate display section 21v includes one display section that provides a display of a value depending on the measured value of, for instance, the second flow rate sensor 39 that will be described below.

The luminal cavity command button 21m plays a role as a command button, for selecting a luminal cavity gas delivery mode in which the gas supply apparatus 45 supplies carbon dioxide gas to the luminal cavity, which when operated, selects the luminal cavity gas delivery mode.

Figure 9:
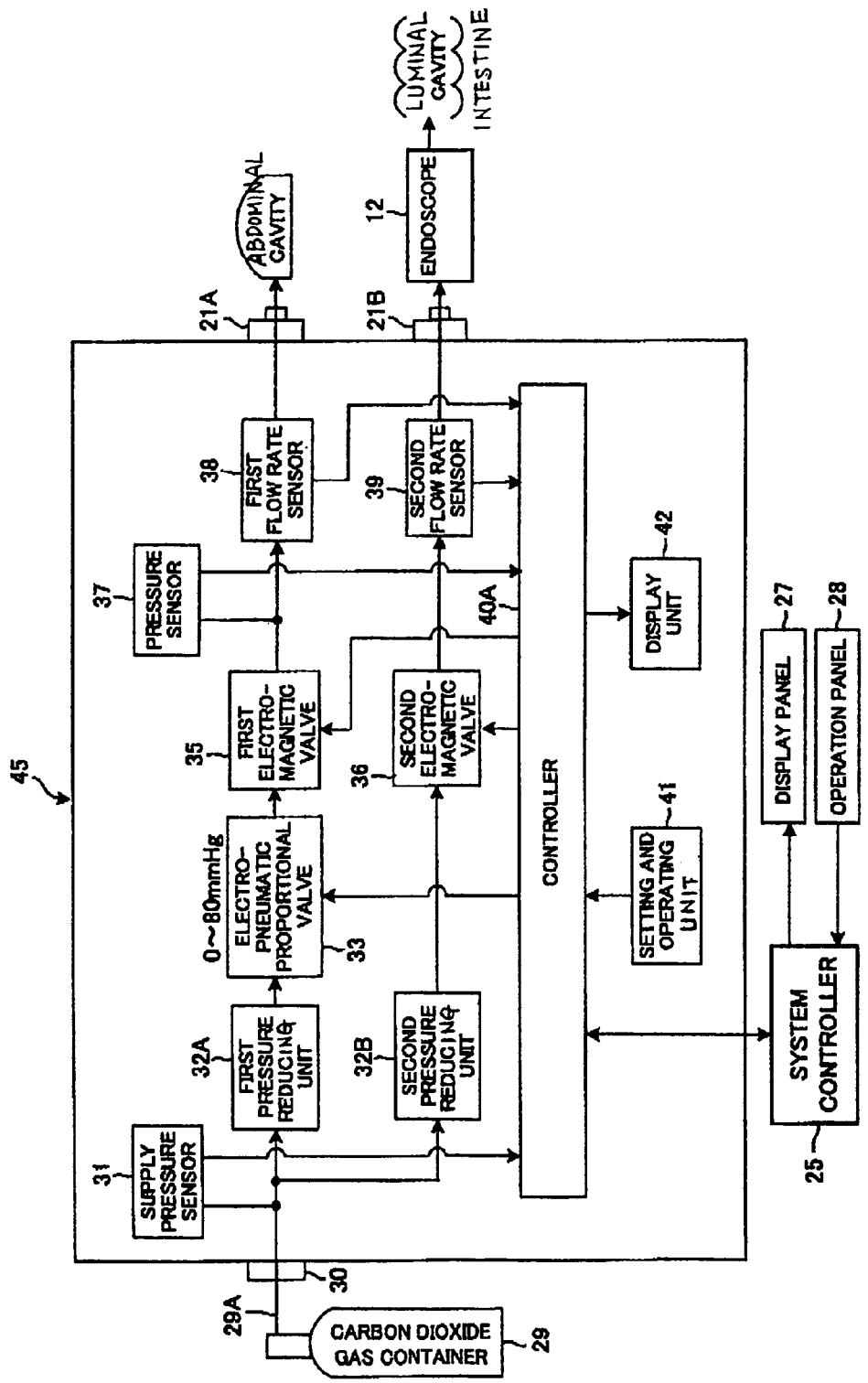
FIG. 9 is a block diagram for illustrating a structure of the gas supply apparatus shown in FIG. 7.

With reference to FIG. 9, a structure of the gas supply apparatus 45 will now be described.

As shown in FIG. 9, the gas supply apparatus 45 is comprised of the high pressure fitting 30, the supply pressure sensor 31, the first pressure reducing unit 32A and electropneumatic proportional valve 33, the second pressure reducing unit 32B, the first and second electromagnetic valves 35, 36, the pressure sensor 37, the first and second flow rate sensors 38 and 39, the controller 40A, the setting and operating unit 41, the display unit 42, an abdominal cavity supply fitting 21A and a luminal cavity supply fitting 21B.

The other end (connector portion) of the abdominal cavity tube 10 is detachably connected to the abdominal cavity supply fitting 21A mounted on the gas supply apparatus 45. The other end (connector portion) of the luminal cavity tube 22 is detachably connected to the luminal cavity supply fitting 21B mounted on the gas supply apparatus 45.

When opening the cock of the carbon dioxide gas container 29, carbon dioxide gas, stored in the carbon dioxide gas container 29 in a liquid form, is vaporized to form carbon dioxide gas that is delivered to internal delivering members formed in two lies for the abdominal cavity and luminal cavity via the internal delivering members disposed inside the gas supply apparatus 45.

Carbon dioxide gas, introduced to the delivering member for the abdominal cavity, is reduced in pressure to a predetermined pressure by the first pressure reducing unit 32A and, then, further regulated in pressure by the electropneumatic proportional valve 33 to a pressure appropriate for supply to an inside of the abdominal cavity upon which carbon dioxide gas is delivered to the abdominal cavity supply fitting 21A via the first electromagnetic valve 35 and first flow rate sensor 38. With the abdominal cavity tube 10 connected to the abdominal cavity supply fitting 21A, carbon dioxide gas is introduced to the inside of the abdominal cavity through the abdominal cavity tube 10 and flow channel (delivering member: not shown) disposed inside the abdominal cavity guide tube 6.

In the meanwhile, carbon dioxide gas, introduced to the delivering member for the luminal cavity, is reduced in pressure by the second pressure reducing unit 32B to a predetermined pressure appropriate for supply to an inside of the luminal cavity and delivered to the luminal cavity supply fitting 21B via the second electromagnetic valve 36 and second flow rate sensor 39. With the luminal cavity tube 22 connected to the luminal cavity supply fitting 21B, carbon dioxide gas is introduced to the flexiblescope 12 via the luminal cavity tube 22, the connector portion 17A and the universal chord 17.

The supply pressure sensor 31 measures the pressure of carbon dioxide gas supplied from the carbon dioxide gas container 29 and outputs the measured result to the controller 40A.

The first pressure reducing unit 32A reduces the pressure of carbon dioxide gas, supplied from the carbon dioxide gas container 29, to the predetermined pressure, upon which carbon dioxide gas is supplied to the electropneumatic proportional valve 33.

The electropneumatic proportional valve 33 is possible to be controlled by the controller 40A such that the pressure of carbon dioxide gas, whose pressure is already reduced by the first pressure reducing unit 32A, is further reduced to a delivery gas pressure in the order of 0 to 80 mmHg appropriate for the abdominal cavity in response to the control signal from the controller 40A.

In the meanwhile, the first pressure reducing unit 32B reduces the pressure of carbon dioxide gas, supplied from the carbon dioxide gas container 29, to another predetermined pressure appropriate for the luminal cavity in a delivery gas pressure range of approximately 100 to 500 mmHg.

The first and second electromagnetic valves 35, 36 serves as the valves, each of which is controllably opened or closed by the controller 40A and switched between a closed and open state depending on a control signal from the controller 40A.

The pressure sensor 37 serves to measure the pressure inside of the abdominal cavity with the first electromagnetic valve 35 being closed, and output the resulting measured value to the controller 40A.

The first flow rate sensor 38 serves to measure the flow rate of carbon dioxide gas passing across the first electromagnetic valve 35 and flowing through the internal delivering member, upon which the resulting measured result is outputted to the controller 40A. The second flow rate sensor 39 serves to measure the flow rate of carbon dioxide gas passing across the second electromagnetic valve 36 and flowing through the internal delivering member, upon which the resulting measured result is outputted to the controller 40A.

Further, although not shown in the drawing figure, the exhaust valve (not shown) may be connected between the first electromagnetic valve 35 and first flow rate sensor 38, like the first embodiment, and opened or closed in response to a control signal from the controller 40A.

Like the first embodiment, the controller 40A is comprised of a computer wherein a CPU (Central Processing Unit) is configured to execute calculations to exhibit various functions. These various functions may include controls, such as pressure control of the electropneumatic proportional valve 33 depending on the detected result of the pressure sensor 37, opening and closing controls of the first and second electromagnetic valves 35, 36 depending on the detected results of the first and second flow rate sensors 38, 39, display control for the display unit 42, gas-delivery start and stop controls in response to operation signals from the setting and operating unit 41, and controls for pressure changes, the flow rate changes, and selections between abdominal cavity and luminal cavity modes.

Now, description is made of the operation of the gas supply apparatus of the second embodiment.

It is supposed that when carrying out laparoscopic surgery, an operator inserts the rigidscope 5 into an inside of an abdominal cavity while inserting the flexiblescope 12 into a luminal cavity, such as the large intestine, to specify a site to be treated for curative treatment.

Upon operation of the operator to manipulate the abdominal cavity command button 21k and gas-delivery start button 21b, the controller 40A regulates the electropneumatic proportional valve 33 to achieve abdominal cavity pressure control to allow the abdominal cavity supply fitting 21A to be supplied with carbon dioxide gas under pressure appropriate for the abdominal cavity in a manner described above.

In contrast, upon operation of the operator to manipulate the luminal cavity command button 21m and gas-delivery start button 21b, the gas supply apparatus 45 allows the luminal cavity supply fitting 21B to be supplied with carbon dioxide gas under pressure appropriate for the luminal cavity in a manner described above.

Before executing the operation, the cock of the carbon dioxide gas container 29 is preliminarily opened in a manner as described above to supply carbon dioxide gas under a high pressure to the gas supply apparatus 45 upon which carbon dioxide gas is introduced through the internal delivering member to the internal delivering members formed in the two lines for the abdominal cavity and luminal cavity.

As set forth above, carbon dioxide gas introduced to the delivering member for the abdominal cavity is reduced in pressure to the predetermined level by the first pressure reducing unit 32A and then further regulated by the electropneumatic proportional valve 33 to the pressure appropriate for supply to the abdominal cavity, upon which carbon dioxide gas is delivered to the abdominal cavity supply fitting 21A through the first electromagnetic valve 35 and first flow rate sensor 38.

On the contrary, carbon dioxide gas introduced to the delivering member for the luminal cavity is reduced in pressure by the second pressure reducing unit 32B to the pressure appropriate for supply to the luminal cavity, upon which carbon dioxide gas is delivered to the luminal cavity supply fitting 21B through the second electromagnetic valve 36 and second flow rate sensor 39.

The gas supply apparatus 45 is also configured such that the abdominal cavity tube 10 is connected to the abdominal cavity supply fitting 21A and the luminal cavity tube 22 is connected to the luminal cavity supply fitting 21B whereby carbon dioxide gas is made possible to be supplied to both the abdominal cavity and luminal cavity.

Figure 10:
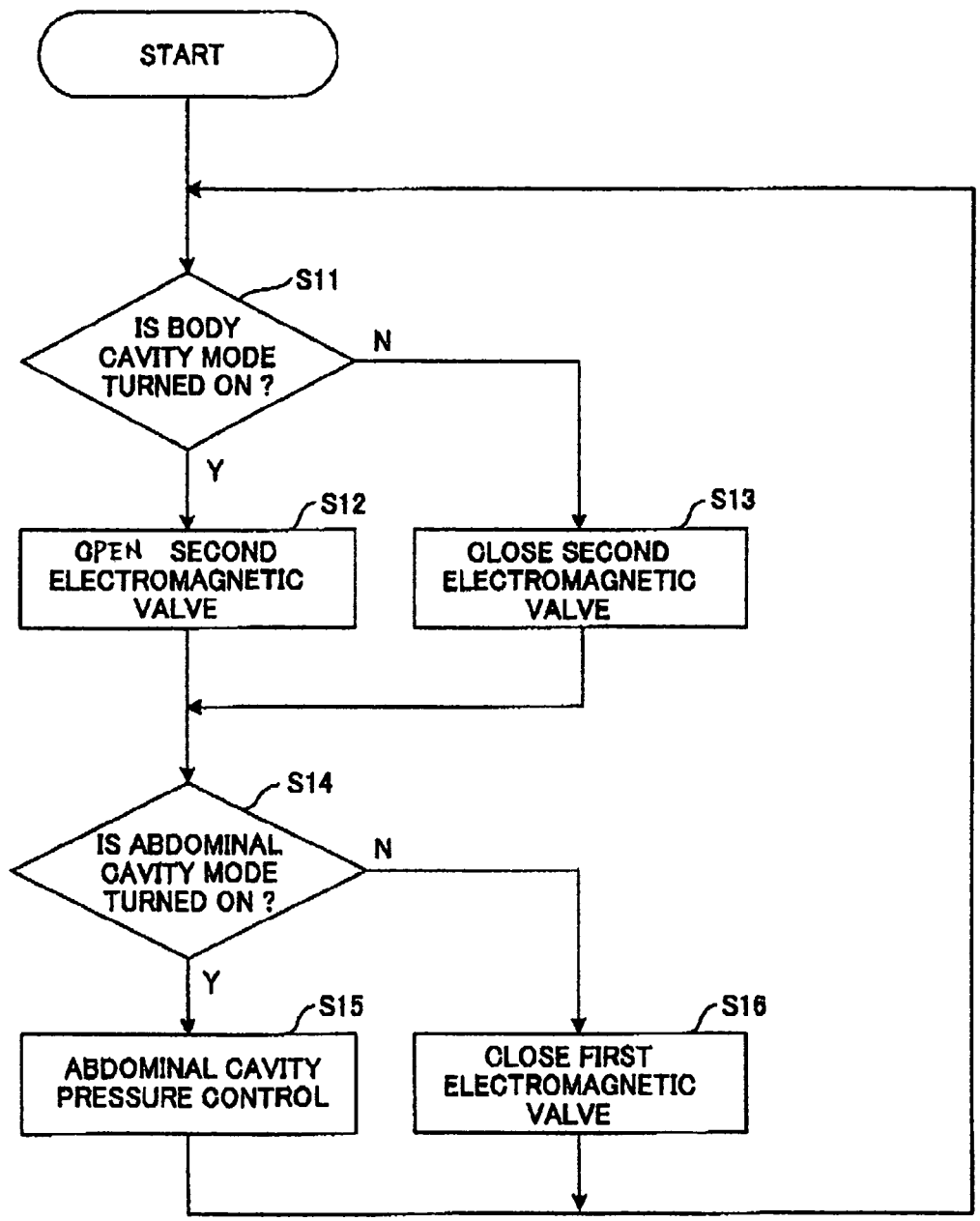
FIG. 10 is a flowchart showing exemplary control operations of a controller shown in FIG. 9.

A basic sequence of operations of the gas supply apparatus 45 of the second embodiment is described further in detail with reference to a flow chart of FIG. 10.

Initially, the controller 40A discriminates whether or not the luminal cavity gas delivery mode is turned on with the luminal cavity command button 21m being operated (step S11). With the luminal cavity gas delivery mode turned on, the controller 40A enters the luminal cavity gas delivery mode. The controller 40A opens the second electromagnetic valve 36 (step S12).

Carbon dioxide gas is supplied from the second pressure reducing unit 32B to the inside of the luminal cavity through the second electromagnetic valve 36, the second flow rate sensor 39, the supply fitting 21B, the luminal cavity tube 22, the connector portion 17A, the universal chord 17 and the flow channel (delivering member: not shown) provided in the flexiblescope 12. Also, with the luminal cavity gas delivery mode turned off, the controller 40A closes the second electromagnetic valve 36 (step S13) and the operation proceeds to next step.

Further, the controller 40A discriminates whether or not the abdominal cavity gas delivery mode is turned on with the abdominal cavity command button 21k being operated (step S14). With the abdominal cavity gas delivery mode turned on, the controller 40A enters the abdominal cavity gas delivery mode. The controller 40A executes abdominal cavity pressure control (step S15).

Carbon dioxide gas, reduced in pressure to the predetermined level by the first pressure reducing unit 32A, is further regulated by the electropneumatic proportional valve 33 operative in response to the control signal from the controller 40A, to a pressure and flow rate appropriate for supply to the abdominal cavity.

Carbon dioxide gas is delivered to the inside of the luminal cavity through the first electromagnetic valve 35, the first flow rate sensor 38, the supply fitting 21A, the abdominal cavity tube 10 and the flow channel (delivering member: not shown) provided in the abdominal cavity guide tube 6.

When this takes place, the first flow rate sensor 38 measures the flow rate of carbon dioxide gas passing across the first electromagnetic valve 35 and flowing through the internal delivering member and outputs the reassured result to the controller 40A. Further, the pressure sensor 37 measures the pressure inside the abdominal cavity, when the first electromagnetic valve 35 is closed, and outputs the measured result to the controller 40A.

Therefore, the controller 40A is responsive to the measured results delivered from the first flow rate sensor 38 and pressure sensor 37 to control the electropneumatic proportional valve 33 so as to perform abdominal cavity pressure control such that carbon dioxide gas, to be supplied to the abdominal cavity, is regulated to the gas delivery pressure in the range of 0 to 80 mmHg and flow rate in the range of 0.1 to 35 L/min appropriate for carbon dioxide gas to be supplied to the abdominal cavity. Moreover, with the abdominal cavity gas delivery mode turned off, the controller 40A closes the first electromagnetic valve 35 (step S16).

After performing abdominal cavity pressure control, the controller 40A allows the operation to return to step S11 and repeatedly execute the operations in steps S11 to S16 until the supply of carbon dioxide is completed.

In this way, the gas supply apparatus 45 of the second embodiment has the same advantageous effects as those of the first embodiment and, in addition, another advantage in that carbon dioxide gas can be simultaneously supplied under pressures appropriate for carbon dioxide gas to be delivered to the abdominal cavity and luminal cavity, respectively. This results in a capability of saving a trouble needed for replacement of the abdominal cavity tube 10 and the luminal cavity tube 22, enabling laborsaving in operations.

Third Embodiment

Figure 11:
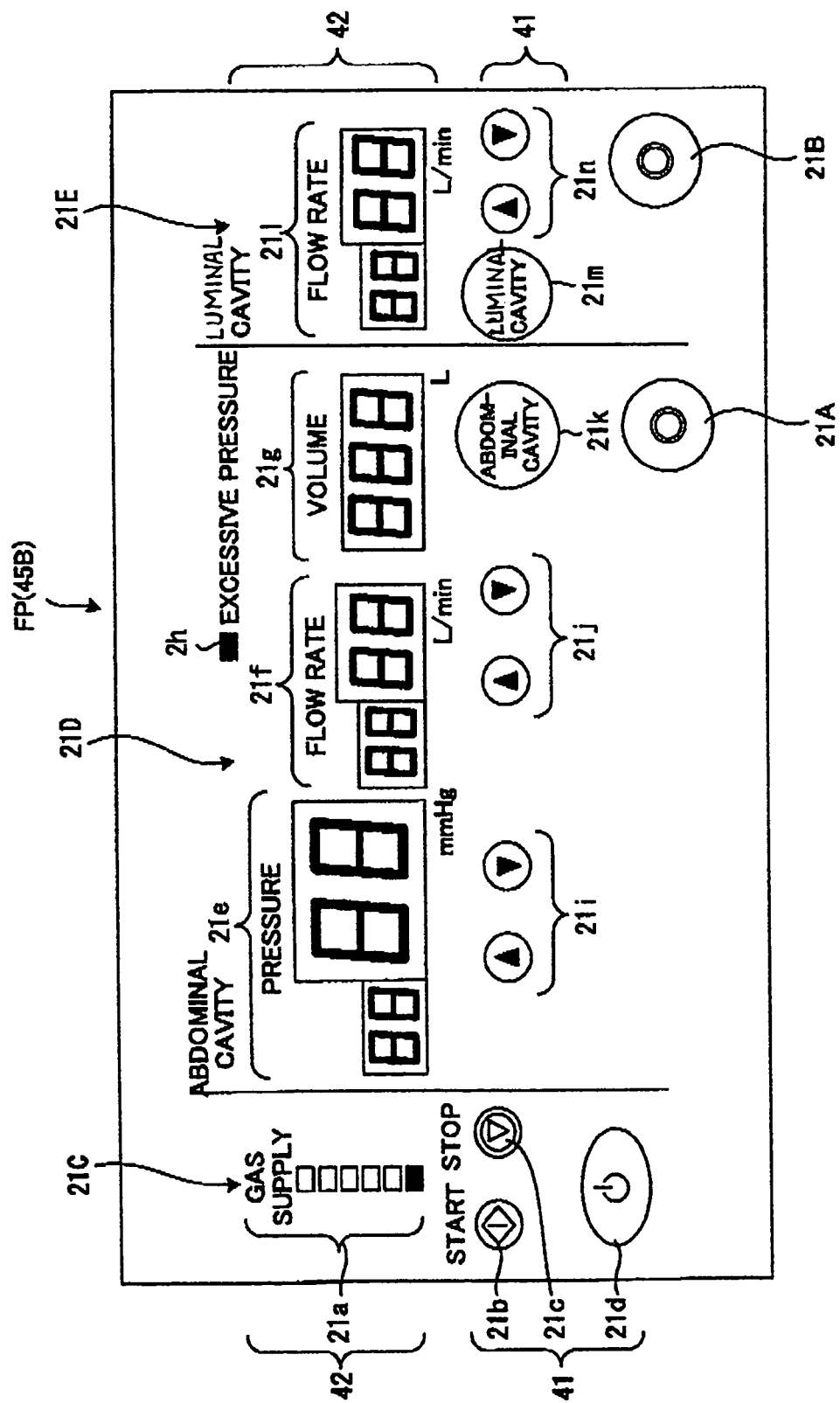
FIG. 11 is a view showing schematic structures of a setting and operating unit and display section of a gas supply apparatus of a third embodiment.
Figure 12:
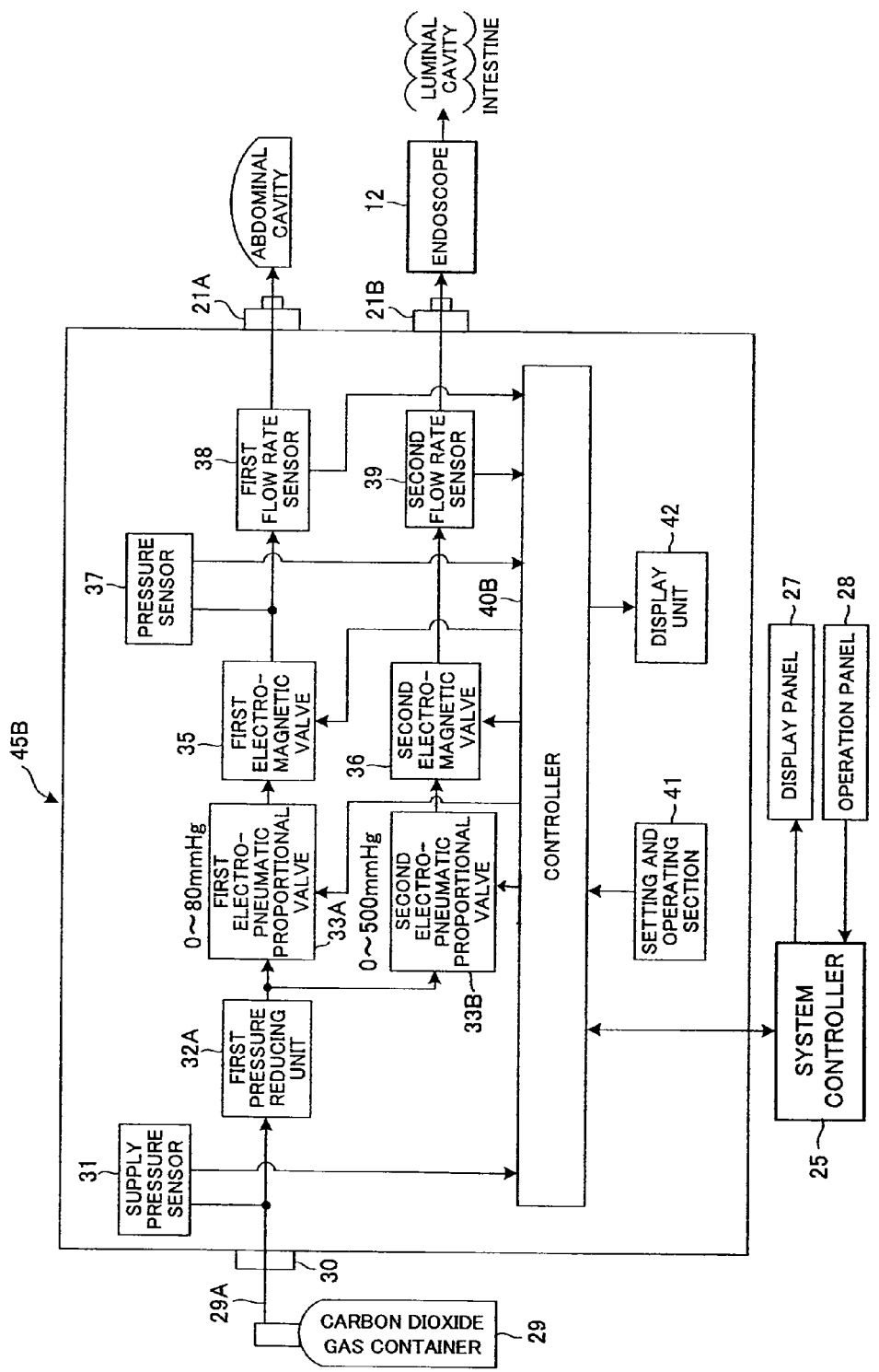
FIG. 12 is a block diagram for illustrating a structure of the gas supply apparatus of the third embodiment.
Figure 13:
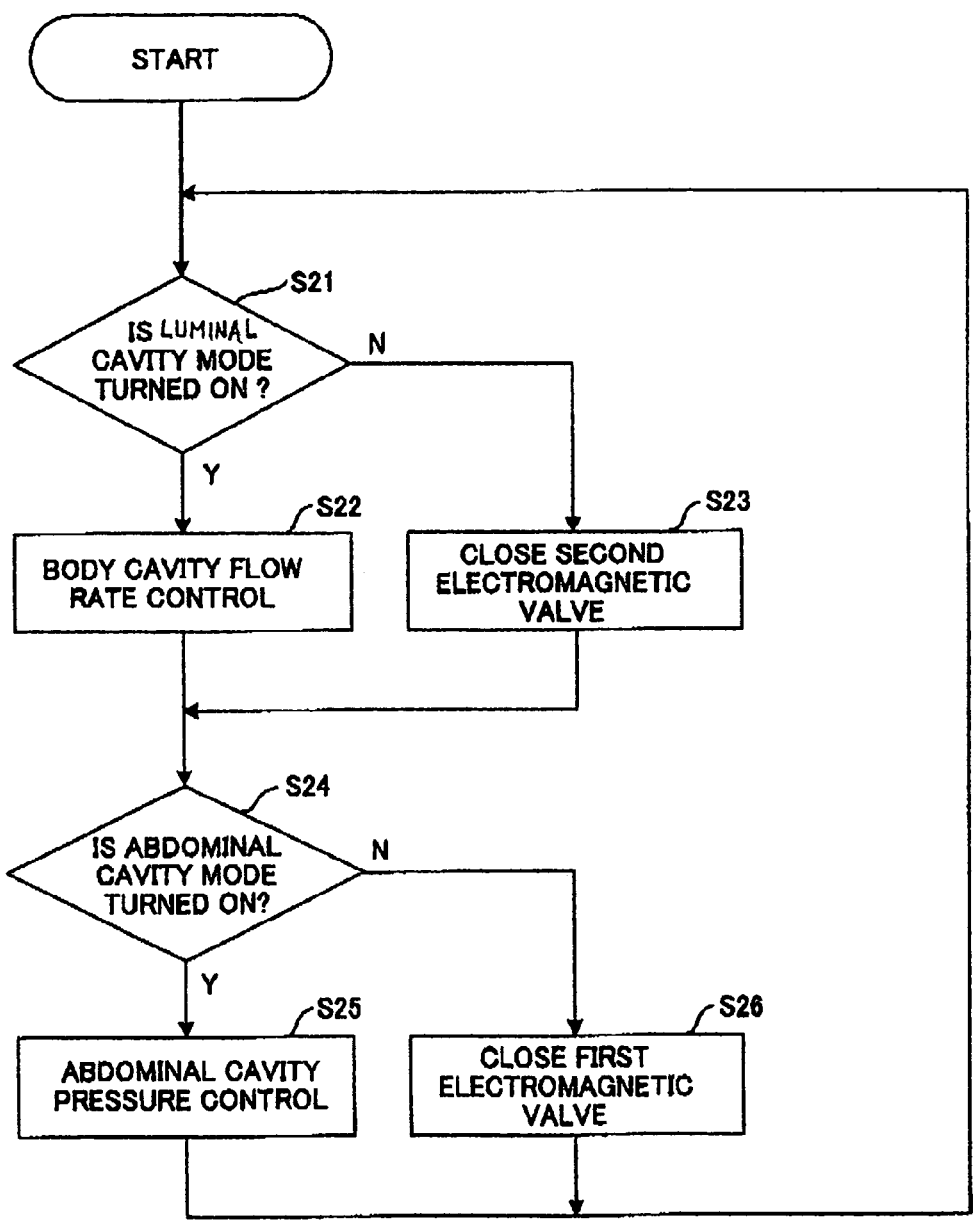
FIG. 13 is a flowchart showing exemplary control operations of a controller shown in FIG. 12.

Referring to FIGS. 11 to 13, a gas supply system of a third embodiment according to the present invention is described. The gas supply system of the third embodiment has a feature in that during operation to supply carbon dioxide gas to a luminal cavity, luminal cavity flow rate control is performed.

First, description is made of a setting and operating section and display section of a gas supply apparatus 45B of the third embodiment.

As shown in FIG. 11, a front panel FP of the gas supply apparatus 45B is provided with a luminal cavity flow rate display section 21*l*, which forms the display unit 42, in the luminal cavity setting and display section 21E.

The luminal cavity flow rate display section 21*l* includes two, left and right display areas wherein the right side display area provides a display of, for instance, a value based on the measured values measured by the second flow rate sensor 39 and the left side display area provides a display of, for instance, a preset flow rate that is preset upon operation of luminal cavity gas delivery flow rate setting buttons 21*n*. Other structures of the setting and operating unit 41 and the display unit 42 are similar to those of the second embodiment and, hence, description of the same is herein omitted.

A structure of the gas supply apparatus 45B will then be described with reference to FIG. 12.

As shown in FIG. 12, the gas supply apparatus 45B is comprised of the high pressure fitting 30, the supply pressure sensor 31, one pressure reducing unit 32, first and second electropneumatic proportional valves 33A and 33B serving as pressure regulators, the first and second electromagnetic valves 35, 36, the pressure sensor 37, the first and second flow rate sensors 38, 39, a controller 40B, the setting and operating unit 41, the display unit 42, the abdominal cavity supply fitting 21A and the luminal cavity supply fitting 21B.

The pressure reducing unit 32 doubles as a pressure regulator means for an abdominal cavity and luminal cavity and the pressure reducing unit 32 cooperates with the first electropneumatic proportional valve 33A to form an abdominal cavity pressure regulator means while the pressure reducing unit 32 cooperates with the second electropneumatic proportional valve 33B to form a luminal cavity pressure regulator means. Moreover, the second electropneumatic proportional valve 33B is configured in a structure wherein a flow rate of carbon dioxide gas is adjusted in a way to supply carbon dioxide gas at a flow rate appropriate for the abdominal cavity.

When opening the cock of the carbon dioxide gas container 29, carbon dioxide gas, stored in the carbon dioxide gas container 29 in a liquid form, is vaporized to form carbon dioxide gas that is delivered to the pressure reducing unit 32 via an internal delivering member located inside the gas supply apparatus 45A. Carbon dioxide gas is reduced in pressure by the pressure reducing unit 32 to a predetermined pressure and, thereafter, introduced to internal delivering members formed in two lines associated with the abdominal cavity and luminal cavity, respectively.

A delivering member for the abdominal cavity is configured to allow carbon dioxide gas to be introduced to an inside of the abdominal cavity via the first electropneumatic proportional valve 33A, the first electromagnetic valve 35, the first flow rate sensor 38, the abdominal cavity supply fitting 21A, the abdominal cavity tube 10 and the flow channel (delivering member: not shown) disposed in the abdominal cavity guide tube 6.

In contrast, a delivering member for the luminal cavity is configured to allow carbon dioxide gas to be introduced to the flexiblescope 12 via the second electropneumatic proportional valve 33B, the second electromagnetic valve 36, the second flow rate sensor 39, the luminal cavity supply fitting 21B, the luminal cavity tube 22, the connector portion 17A and the universal chord 17.

The supply pressure sensor 31 measures the pressure of carbon dioxide gas, supplied from the carbon dioxide gas container 29, and the measured result is outputted to the controller 40B. The pressure reducing unit 32 reduces the pressure of carbon dioxide gas, supplied from the carbon dioxide gas container 29, to a predetermined pressure, upon which carbon dioxide gas is supplied to the first and second electropneumatic proportional valves 33A and 33B.

The first electropneumatic proportional valve 33A is possible to be controlled by the controller 40B such that the pressure of carbon dioxide gas, reduced by the pressure reducing unit 32, is further reduced to a delivery gas pressure in the order of 0 to 80 mmHg appropriate for the abdominal cavity in response to a control signal from the controller 40B.

In the meanwhile, the second electropneumatic proportional valve 33B is possible to be controlled by the controller 40B such that the pressure of carbon dioxide gas, reduced by the pressure reducing unit 32, is further reduced to a delivery gas pressure in the order of 100 to 500 mmHg appropriate for the luminal cavity in response to a control signal from the controller 40B.

The first and second electromagnetic valves 35, 36 serves as the valves, each of which is controllably opened or closed by the controller 40B and switched between a closed and open state depending on a control signal from the controller 40B.

The pressure sensor 37 serves to measure the pressure inside of the abdominal cavity with the first electromagnetic valve 35 being closed, and output the resulting measured value to the controller 40B.

The first flow rate sensor 38 serves to measure the flow rate of carbon dioxide gas passing across the first electromagnetic valve 35 and flowing through the internal delivering member, upon which the resulting measured result is outputted to the controller 40B. The second flow rate sensor 39 serves to measure the flow rate of carbon dioxide gas passing across the second electromagnetic valve 36 and flowing through the internal delivering member, upon which the resulting measured result is outputted to the controller 40B.

Further, although not shown in the drawing figure, like the first and second embodiments, the exhaust valve (not shown) may be connected between the first electromagnetic valve 35 and first flow rate sensor 38 and opened or closed in response to a control signal from the controller 40B.

The controller 40B is comprised of a computer, like the first and second embodiments, in which a CPU is configured to execute given calculations to exhibit various functions. These various functions may include controls, such as pressure controls of the first and second electropneumatic proportional valves 33A and 33B depending on the detected result of the pressure sensor 37, opening and closing control of the first electromagnetic valve 35 depending on the detected result of the first flow rate sensor 38, opening and closing control of the second electromagnetic valves 36 and opening and closing control of the second electromagnetic valves 36 depending on the detected result of the second flow rate sensor 39, display control for the display unit 42, and controls for start and stop of gas delivery, change of pressures, change of flow rates and selection for the abdominal cavity and luminal cavity modes.

Description will now be made of the operation of the gas supply apparatus 45B of the third embodiment.

It is supposed that when carrying out laparoscopic surgery, an operator inserts the rigidscope 5 into the inside of the abdominal cavity while inserting the flexiblescope 12 into the luminal cavity, such as the large intestine, to specify a site to be treated for curative treatment.

Upon operation of the operator to depress the abdominal cavity command button 21k and gas-delivery start button 21b, the gas supply apparatus 45B regulates the first electropneumatic proportional valve 33A to achieve abdominal cavity pressure control to allow the supply fitting 21A to be supplied with carbon dioxide gas under pressure appropriate for the abdominal cavity in a manner described above.

In the meantime, upon operation of the operator to operate the luminal cavity command button 21m and gas-delivery start button 21b, the gas supply apparatus 45B regulates the second electropneumatic proportional valve 33B to achieve luminal cavity pressure control to allow the luminal cavity supply fitting 21B to be supplied with carbon dioxide gas under pressure appropriate for the luminal cavity in a manner described above.

As used herein, the term "luminal cavity flow rate control" refers to control in that when the second electromagnetic valve 36 is opened to supply carbon dioxide gas, the opening degree of the second electropneumatic proportional valve 33B is controlled depending on the measured result resulting from the second flow rate sensor 39 for thereby controlling the flow rate of carbon dioxide gas to a preset value.

Before executing the operation, the cock of the carbon dioxide gas container 29 is preliminarily opened in a manner as described above to supply carbon dioxide gas under a high pressure to the gas supply apparatus 45B upon which carbon dioxide gas is introduced through the internal delivering member to the pressure reducing unit 32 by which carbon dioxide gas is reduced in pressure to a predetermined level.

The operation of the gas supply apparatus 45B of the third embodiment is described further in detail with reference to a flow chart of FIG. 13.

Initially, the controller 40B discriminates whether or not the luminal cavity gas delivery mode is turned with the luminal cavity command button 21m being operated (step S21). With the luminal cavity gas delivery mode turned on, the controller 40B enters the luminal cavity gas delivery mode for achieving luminal cavity flow rate control (step S22).

Carbon dioxide gas, whose pressure is reduced to the predetermined pressure by the pressure reducing unit 32, is further regulated to a pressure and gas delivery flow rate appropriate for the luminal cavity by the second electropneumatic proportional valve 33B and introduced to the luminal cavity through the second electromagnetic valve 33B, the second flow rate sensor 39, the luminal cavity supply fitting 21B, the luminal cavity tube 22, the connector portion 17A, the universal chord 17 and the flow channel (delivering member: not shown) provided in the flexiblescope 12.

When this takes place, the second flow rate sensor 39 measures the flow rate of carbon dioxide gas passing across the second electromagnetic valve 36 and flowing through the internal delivering member and outputs the reassured result to the controller 40B. The controller 40B is responsive to this measured result to control the second electropneumatic proportional valve 33B in a way to achieve luminal cavity flow rate control so as to control the flow rate of carbon dioxide gas, to be supplied to the luminal cavity, to a range of 1 to 3 L/min appropriate for supplying carbon dioxide gas to the luminal cavity. Also, with the luminal cavity gas delivery mode turned off, the controller 40B closes the second electromagnetic valve 36 (step S23) and allows the operation to proceed to subsequent step.

Further, the controller 40B discriminates whether or not the abdominal cavity gas delivery mode is turned on upon operation of the abdominal cavity command button 21k (step S24). With the abdominal cavity gas delivery mode turned on, the controller 40B enters the abdominal cavity gas delivery mode for achieving abdominal cavity pressure control (step S25).

Carbon dioxide gas, whose pressure is reduced to the predetermined pressure by the pressure reducing unit 32, is further regulated to a pressure and a gas delivery flow rate appropriate for the abdominal cavity by the first electropneumatic proportional valve 33A controlled in response to a control signal from the controller 40B.

Carbon dioxide gas, whose pressure is reduced to the predetermined pressure by the pressure reducing unit 32, is further regulated to a pressure and a gas delivery flow rate appropriate for the abdominal cavity by the first electropneumatic proportional valve 33A and introduced to the abdominal cavity through the first electromagnetic valve 33A, the first flow rate sensor 38, the abdominal cavity supply fitting 21A, the abdominal cavity tube 10 and the flow channel (delivering member: not shown) provided in the abdominal cavity guide tube 6.

When this takes place, the first flow rate sensor 38 measures the flow rate of carbon dioxide gas passing across the first electromagnetic valve 35 and flowing through the internal delivering member and outputs the reassured result to the controller 40B. Also, the pressure sensor 37 measures the pressure in the abdominal cavity when the first electromagnetic valve 35 and outputs the measured result to the controller 40B.

The controller 40B is responsive to the measured results of the first flow rate sensor 38 and pressure sensor 37 to control the first electropneumatic proportional valve 33A in a way to achieve abdominal cavity flow rate control so as to control the pressure and flow rate of carbon dioxide gas, to be supplied to the abdominal cavity, to a range of 0 to 80 mmHg and a range of 0.1 to 35 L/min appropriate for supplying carbon dioxide gas to the abdominal cavity. Also, with the abdominal cavity gas delivery mode turned off, the controller 40B closes the first electromagnetic valve 35 (step S26) and allows the operation to proceed to subsequent step.

Moreover, subsequent to luminal cavity flow rate control and abdominal cavity pressure control, the controller 40B allows the operation to return to step S21 to repeatedly execute the operations in steps S21 to S26.

Thus, the gas supply apparatus 45B of the third embodiment operates in a way to supply carbon dioxide gas to the abdominal cavity under the pressure appropriate for the abdominal cavity due to abdominal cavity pressure control executed by the first electropneumatic proportional valve 33A controlled by the controller 40B while carbon dioxide gas is supplied to the luminal cavity at the flow rate appropriate for the luminal cavity due to luminal cavity flow rate control executed by the second electropneumatic proportional valve 33B controlled by the controller 40B.

Accordingly, the third embodiment has the same advantageous effects as those of the second embodiment mentioned above and, in addition, has a capability of performing luminal cavity flow rate control for thereby enabling delivery of carbon dioxide gas in a manner further appropriate for gas delivery to the luminal cavity.

As set forth above, the gas supply systems of the various embodiments set forth above are made possible to execute abdominal-cavity gas delivery and luminal-cavity gas delivery under pressures suited for the abdominal cavity and luminal cavity, respectively, in structures that are small in size and low in costs, thereby enabling effective utilization of spaces in operation rooms. Further, the gas supply systems of the presently filed embodiments are particularly effective when executing curative treatment upon inserting the rigidscope in the abdominal cavity while inserting the flexiblescope to the luminal cavity, such as the large intestine, for specifying the site for curative treatment during laparoscopic surgery.

In addition, the present invention is not limited to particular structures of the first to third embodiments set forth above and may be implemented in various modified forms without departing from the spirit and scope of the present invention.

What is claimed is:

1. A gas supply system for supplying gas to a patient, the gas supply system comprising:
   a source of gas adapted to supply insufflation gas of a predetermined kind;
   a first delivering path that delivers the gas to be insufflated into an abdominal cavity of the patient;
   a second delivering path that delivers the gas to be insufflated into a luminal cavity of the patient;
   a first pressure regulating block arranged in the first delivering path to regulate a pressure of the gas, supplied from the source of gas, at a pressure level proper for supply of the gas to the abdominal cavity, wherein the first pressure regulating block comprises a first pressure reducing unit that reduces the pressure of the gas from the source of gas down to a first pressure level and a first pressure regulator that regulates the pressure of the gas from the first pressure reducing unit at the pressure level proper for the supply of the gas to the abdominal cavity in response to control performed on information indicative of a state of the gas flowing through the first delivering path;
   a second pressure regulating block arranged in the second delivering path to regulate the pressure of the gas, supplied from the source of gas, at a pressure level proper for supply of the gas to the luminal cavity, wherein the second pressure regulating block comprises a second pressure reducing unit that reduces the pressure of the gas from the source of gas down to a second pressure level and a second pressure regulator that regulates the pressure of the gas from the second pressure reducing unit at the pressure level proper for the supply of the gas to the luminal cavity in response to control performed on information indicative of a state of the gas flowing through the second delivering path;
   a switchover device that performs a selective switchover between i) supply of the gas of which pressure is regulated to be proper for the abdominal cavity and which is delivered through the first delivering path and ii) supply of the gas of which pressure is regulated to be proper for the luminal cavity and which is delivered through the second delivering path;
   a controller that controls operations of the first and second pressure regulators and the switchover device based on the information indicative of a state of the as flowing through the first and second delivering paths; and
   a single gas supply port that receives the gas from the switchover device and supplies the received gas outside the gas supply system,
   wherein the source of gas is a source of insufflation gas of one kind,
   wherein the second pressure regulating block comprises
   a second electromagnetic valve disposed after the second pressure reducing unit in the second delivering path to selectively open and close the second delivering path to interrupt the flow of the gas passing through the second delivering path; and
   a second flow rate sensor disposed in the second delivering path for detecting a flow rate of the gas flowing through the second delivering path, the flow rate of the gas flowing through the second delivering path being included in the information indicative of the state of the gas flowing therethrough, wherein
   the controller is adapted to control opening and closing operations of the second electromagnetic valve depending on information indicative of the flow rate detected by the second flow rate sensor.

2. A gas supply system for supplying gas to a patient, the gas supply system comprising:
   a source of gas adapted to supply insufflation gas of a predetermined kind;
   a pressure reducing unit that reduces a pressure of the gas supplied from the source of gas down to a predetermined pressure level;
   a first delivering path that is connected to an output of the pressure reducing unit and that delivers the gas to be insufflated into an abdominal cavity of the patient;
   a second delivering path that is connected to the output of the pressure reducing unit such that the first and second delivering paths are parallel with each other, and that delivers the gas to be insufflated into a luminal cavity of the patient;
   a first pressure regulating block which is arranged in the first delivering path and which comprises a first pressure regulator that regulates the pressure of the gas from the pressure reducing unit at a pressure level proper for the supply of the gas to the abdominal cavity in response to control performed on information indicative of a state of the gas flowing through the first delivering path;
   a second pressure regulating block which is arranged in the second delivering path and which comprises a second pressure regulator that regulates the pressure of the gas from the pressure reducing unit at a pressure level proper for supply of the gas to the luminal cavity in response to control performed on information indicative of a state of the gas flowing through the second delivering path; and
   a controller that controls operations of the first and second pressure regulators based on the information indicative of the gas flowing through the first and second delivering paths, wherein the source of gas is a source of insufflation gas of one kind;

the first pressure regulator comprises
a first electro-pneumatic proportional valve that is disposed in the first delivering path and regulates the pressure of the gas flowing therethrough, and
a first electromagnetic valve disposed after the first electro-pneumatic proportional valve in the first delivering path to selectively open and close to interrupt a flow of the gas passing through the first delivering path;

the first pressure regulating block comprises
a pressure sensor disposed after the first electromagnetic valve in the first delivering path to detect the pressure of the gas inside the abdominal cavity in cases where the first electromagnetic valve is closed, and the controller is adapted to repeatedly control operations of the first electro-pneumatic proportional valve, the first electromagnetic valve, and the pressure sensor based on the pressure of the gas detected, as the information indicative of the state of the gas flowing through the first delivering path, by the pressure sensor so that the gas detected by the pressure sensor is kept at the pressure level proper for the supply of the gas to the abdominal cavity.

3. The gas supply system according to claim 2, wherein
the first electro-pneumatic proportional valve is a valve to which a first desired pressure level is given by an operator, and
the second pressure regulator comprises a second electro-pneumatic proportional valve to which a second desired pressure is given by the operator.

4. The gas supply system according to claim 3, further comprising:
a panel having a front surface which is accessible by the operator; and
first and second gas supply ports that are provided on the front surface of the panel and connected to the first and second delivering paths respectively so that the gas from the first and second delivering paths is supplied outside the gas supply system via the first and second gas supply ports respectively, the first and second gas supply ports being connectable with tubes being connected to the abdominal and luminal cavities.

5. The gas supply system according to claim 3, wherein
the second pressure regulator comprises
a second electromagnetic valve disposed after the second electro-pneumatic proportional valve in the second delivering path to selectively open and close the second delivering path to interrupt the flow of the gas passing through the second delivering path;

the second pressure regulating block further comprises
a second flow rate sensor disposed in the second delivering path for detecting a flow rate of the gas flowing through the second delivering path, the flow rate of the gas flowing through the second delivering path being included in the information indicative of the state of the gas flowing therethrough; and the controller is adapted to control opening and closing operations of the second electromagnetic valve depending on information indicative of the flow rate detected by the second flow rate sensor.

6. The gas supply system according to claim 5, further comprising:
a first gas supply port connected to an output end of the first delivering path and used to be connected to the abdominal cavity of the patient; and a second gas supply port connected to an output end of the second delivering path and used to be connected to the luminal cavity of the patient.

7. The gas supply system according to claim 6, wherein
the first gas supply port is adapted to be connected with a first tube delivering the gas supplied from the first gas supply port, to the abdominal cavity of the patient using a rigidscope, and
the second gas supply port is adapted to be connected with a second tube delivering the gas supplied from the second gas supply port, to the luminal cavity of the patient using a flexiblescope.

8. The gas supply system according to claim 4, further comprising a display unit that is provided on the front surface of the panel and provides the display unit with information indicative of the state of the gas supplied to the abdominal and luminal cavities.

9. A gas supply system for supplying gas to a patient, the gas supply system comprising:
a source of gas adapted to supply insufflation gas of a predetermined kind;
a first delivering path that delivers the gas to be insufflated into an abdominal cavity of the patient;
a second delivering path that delivers the gas to be insufflated into a luminal cavity of the patient;
a first pressure regulating block arranged in the first delivering path to regulate a pressure of the gas, supplied from the source of gas, at a pressure level proper for supply of the gas to the abdominal cavity, wherein the first pressure regulating block comprises a first pressure reducing unit that reduces the pressure of the gas from the source of gas down to a first pressure level and a first pressure regulator that regulates the pressure of the gas from the first pressure reducing unit at the pressure level proper for the supply of the as to the abdominal cavity in response to control performed on information indicative of a state of the gas flowing through the first delivering path;
a second pressure regulating block arranged in the second delivering path to regulate the pressure of the as su lied from the source of as at a pressure level proper for supply of the gas to the luminal cavity, wherein the second pressure regulating block comprises a second pressure reducing unit that reduces the pressure of the gas from the source of gas down to a second pressure level and a second pressure regulator that regulates the pressure of the gas from the second pressure reducing unit at the pressure level proper for the supply of the gas to the luminal cavity in response to control performed on information indicative of a state of the gas flowing through the second delivering path;
a switchover device that performs a selective switchover between i) supply of the gas of which pressure is regulated to be proper for the abdominal cavity and which is delivered through the first delivering path and ii) supply of the gas of which pressure is regulated to be proper for the luminal cavity and which is delivered through the second delivering path;
a controller that controls operations of the first and second pressure regulators and the switchover device based on the information indicative of a state of the gas flowing through the first and second delivering paths; and
a single gas supply port that receives the gas from the switchover device and supplies the received gas outside the gas supply system,
wherein the source of gas is a source of insufflation gas of one kind, wherein the first pressure regulator is an electro-pneumatic proportional valve that is disposed after the first pressure reducing unit in the first delivering path and that regulates the pressure of the gas reduced by the first pressure reducing unit at the first pressure level selected from a desired pressure range based on the information indicative of the state of the gas flowing through the first delivering path.

10. The gas supply system according to claim 9, wherein the first pressure regulating block comprises
a first electromagnetic valve disposed after the electro-pneumatic proportional valve in the first delivering path to selectively open and close the first delivering path to interrupt a flow of the gas passing through the first delivering path; and
a first flow rate sensor disposed in the first delivering path for detecting a flow rate of the gas passing through the first delivering path, the flow rate being included in the information indicative of the state of the gas flowing through the first delivering path, wherein
the controller is adapted to control opening and closing operations of the first electromagnetic valve depending on information indicative of the flow rate detected by the first flow rate sensor.

11. The gas supply system according to claim 10, wherein the second pressure regulating block comprises
a second electromagnetic valve disposed after the second pressure reducing unit in the second delivering path to selectively open and close the second delivering path to interrupt the flow of the gas passing through the second delivering path; and
a second flow rate sensor disposed in the second delivering path for detecting a flow rate of the gas flowing through the second delivering path, the flow rate of the gas flowing through the second delivering path being included in the information indicative of the state of the gas flowing therethrough, wherein
the controller is adapted to control opening and closing operations of the second electromagnetic valve depending on information indicative of the flow rate detected by the second flow rate sensor.

12. The gas supply system according to claim 10, wherein the first pressure regulating block further comprises
a pressure sensor disposed after the first electromagnetic valve in the first delivering path to detect the pressure of the gas inside the abdominal cavity in cases where the first electromagnetic valve is closed, wherein
the controller is adapted to repeatedly control operations of the electro-pneumatic proportional valve, the first electromagnetic valve, and the pressure sensor based on the pressure of the gas detected by the pressure sensor so that the gas detected, as the information indicative of the state of the gas flowing through the first delivering path, by the pressure sensor is kept at the first pressure level.

13. A gas supply system for supplying gas to a patient, the gas supply system comprising:
a source of gas adapted to supply insufflation gas of a predetermined kind;
a pressure reducing unit that reduces a pressure of the gas supplied from source of gas down to a predetermined pressure level;
a first delivering path that is connected to an output of the pressure reducing unit and that delivers the gas to be insufflated into an abdominal cavity of the patient;
a second delivering path that is connected to the output of the pressure reducing unit such that the first and second delivering paths are parallel with each other, and that delivers the gas to be insufflated into a luminal cavity of the patient;
a first pressure regulating block which is arranged in the first delivering path and which comprises a first pressure regulator that regulates the pressure of the gas from the pressure reducing unit at a pressure level proper for the supply of the gas to the abdominal cavity in response to control performed on information indicative of a state of the gas flowing through the first delivering path;
a second pressure regulating block which is arranged in the second delivering path and which comprises a second pressure regulator that regulates the pressure of the gas from the pressure reducing unit at a pressure level proper for supply of the gas to the luminal cavity in response to control performed on information indicative of a state of the gas flowing through the second delivering path; and
a controller that controls operations of the first and second pressure regulators based on the information indicative of the gas flowing through the first and second delivering paths,
wherein the source of gas is a source of insufflation gas of one kind;
the first pressure regulator comprises
a first electro-pneumatic proportional valve that is disposed in the first delivering path and regulates the pressure of the gas flowing therethrough, and
a first electromagnetic valve disposed after the first electro-pneumatic proportional valve in the first delivering path to selectively open and close the first delivering path to interrupt a flow of the gas passing through the first delivering path;
the first pressure regulating block comprises
a first flow rate sensor disposed in the first delivering path for detecting a flow rate of the gas passing through the first delivering path, the flow rate of the gas flowing through the first delivering path being included in the information indicative of the state of the gas flowing therethrough; and
the controller is adapted to control opening and closing operations of the first electromagnetic valve depending on information of the flow rate detected by the first flow rate sensor.

14. The gas supply system according to claim 13, wherein the first pressure regulating block further comprises
a pressure sensor disposed after the first electromagnetic valve in the first delivering path to detect the pressure of the gas inside the abdominal cavity in cases where the first electromagnetic valve is closed,
wherein the controller is adapted to repeatedly control operations of the first electro-pneumatic proportional valve, the first electromagnetic valve, and the pressure sensor based on the pressure of the gas detected by the pressure sensor so that the gas detected, as the information indicative of the state of the gas flowing through the first delivering path, by the pressure sensor is kept at the pressure level proper for the supply of the gas to the abdominal cavity.

15. The gas supply system according to claim 13, comprising:
a first gas supply port that connects the first delivering path and a first tube communicating with the abdominal cavity of the patient using a rigidscope so that the gas supplied through the first delivering path reaches the abdominal cavity via the first gas supply port and the first tube; and a second gas supply port that connects the second delivering path and a second tube communicating with a flexiblescope inserted into the luminal cavity of the patient so that the gas supplied through the second delivering path reaches the luminal cavity via the second gas supply port, the second port, and the flexiblescope.

* * * * *